(12) United States Patent
Kuwano et al.

(10) Patent No.: US 12,026,880 B2
(45) Date of Patent: Jul. 2, 2024

(54) FLUORESCENCE IMAGE DISPLAY METHOD AND FLUORESCENCE IMAGE ANALYZER

(71) Applicant: SYSMEX CORPORATION, Kobe (JP)

(72) Inventors: Keisuke Kuwano, Kobe (JP); Chikako Murata, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 124 days.

(21) Appl. No.: 17/560,924

(22) Filed: Dec. 23, 2021

(65) Prior Publication Data
US 2022/0207725 A1 Jun. 30, 2022

(30) Foreign Application Priority Data
Dec. 24, 2020 (JP) ................................. 2020-215595

(51) Int. Cl.
*G06T 7/00* (2017.01)
*A61B 5/00* (2006.01)
*G06T 11/00* (2006.01)

(52) U.S. Cl.
CPC .......... *G06T 7/0012* (2013.01); *A61B 5/0071* (2013.01); *G06T 11/001* (2013.01);
(Continued)

(58) Field of Classification Search
CPC ................. G06T 7/0012; G06T 11/001; G06T 2207/20221; G06T 2207/10024;
(Continued)

(56) References Cited

U.S. PATENT DOCUMENTS

2007/0166749 A1 7/2007 Palanisamy et al.
2014/0072195 A1* 3/2014 Zhang .................. G06V 20/698
382/129
(Continued)

FOREIGN PATENT DOCUMENTS

| EP | 3492907 A1 | 6/2019 |
|----|-----------|--------|
| JP | 2017-80855 A | 5/2017 |
| JP | 2018-174828 A | 11/2018 |

OTHER PUBLICATIONS

Extended European search report dated May 20, 2022 in European patent application No. 21216377.8.
"Second Edition of Guidelines for Quality Assurance of Chromosomal and Genetic Testing", The Official Journal of the Japanese Association for Chromosome and Gene Analysis, The Japanese Association for Chromosome and Gene Analysis, Apr. 2014, vol. 32, No. 1, pp. 60-89.
Communication pursuant to Article 94(3) EPC issued on May 22, 2024 in a counterpart European patent application No. 21216377.8, 6 pages.

*Primary Examiner* — Xilin Guo
(74) *Attorney, Agent, or Firm* — Crowell & Moring LLP

(57) ABSTRACT

A fluorescence image display method and a fluorescence image analyzer capable of suppressing the influence of the operator's skill level and improving the classification accuracy when an operator visually classifies cells is provided. A fluorescence image analyzer, which is an example of an embodiment, includes a light source that irradiates light on a cell having a target site labeled with a fluorescent dye, an imaging unit that acquires a fluorescence image of a cell which emits fluorescence via irradiation by light, and a processing unit that analyzes the fluorescence image by software based on the fluorescence bright spot of the fluorescence image. The processing unit is configured to display a fluorescence image of the cell, the result of the image analysis, and auxiliary information that assists the visual analysis of the fluorescence bright spot included in the fluorescence image.

23 Claims, 21 Drawing Sheets

(52) U.S. Cl.
CPC . *A61B 2576/00* (2013.01); *G06T 2207/10024* (2013.01); *G06T 2207/10064* (2013.01); *G06T 2207/20021* (2013.01); *G06T 2207/20221* (2013.01)

(58) Field of Classification Search
CPC . G06T 2207/20021; G06T 2207/10064; G06T 2207/30024; G06T 7/11; G06V 20/698; G06V 10/56; G06V 20/695; G06F 18/251; A61B 5/0071; A61B 2576/00; A61B 5/0059; A61B 1/043; G01N 21/6428; G01N 21/6458
See application file for complete search history.

(56) References Cited

U.S. PATENT DOCUMENTS

| | | | | |
|---|---|---|---|---|
| 2016/0202465 A1* | 7/2016 | Sase | ............... | G01N 21/6458 382/164 |
| 2018/0299382 A1* | 10/2018 | Yamada | ............ | C12Q 1/6841 |
| 2018/0372636 A1* | 12/2018 | Sofue | ................. | G06T 7/0014 |
| 2021/0030266 A1* | 2/2021 | Hirokawa | ............ | G06T 11/206 |

* cited by examiner

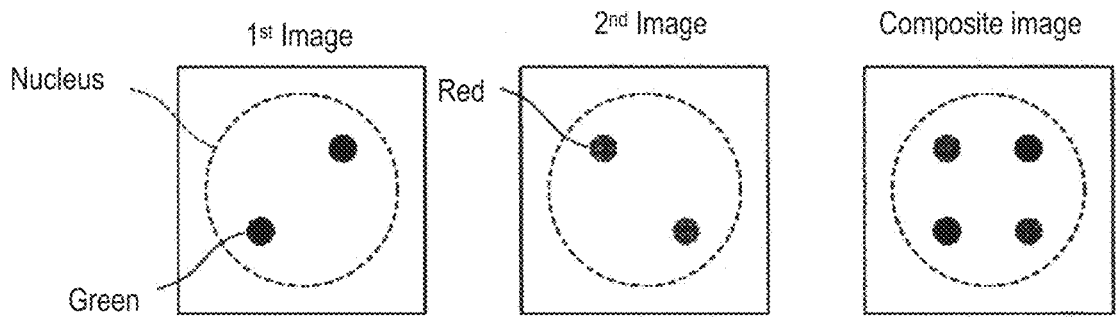
FIG. 3A Negative pattern
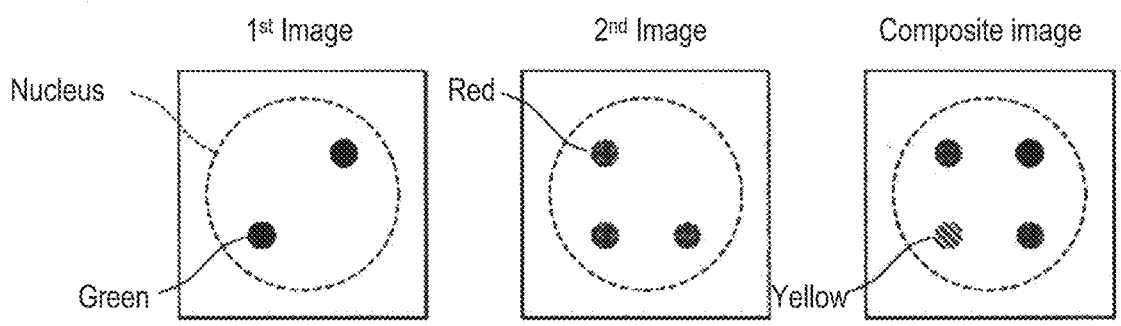
FIG. 3B Positive pattern 1
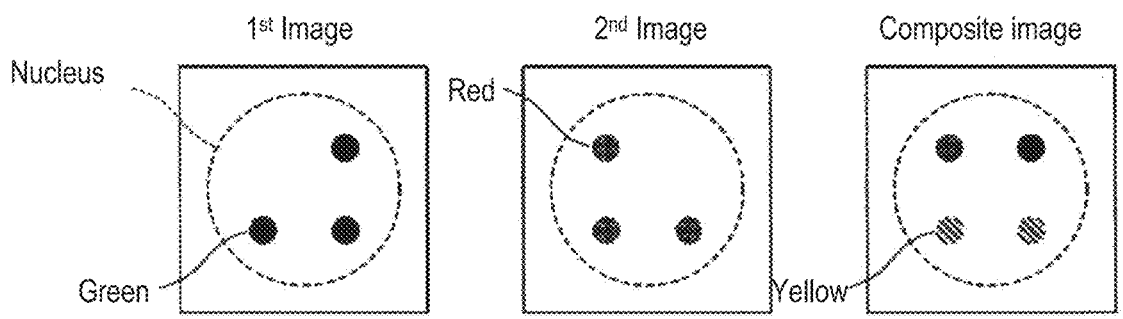
FIG. 3C Positive pattern 2
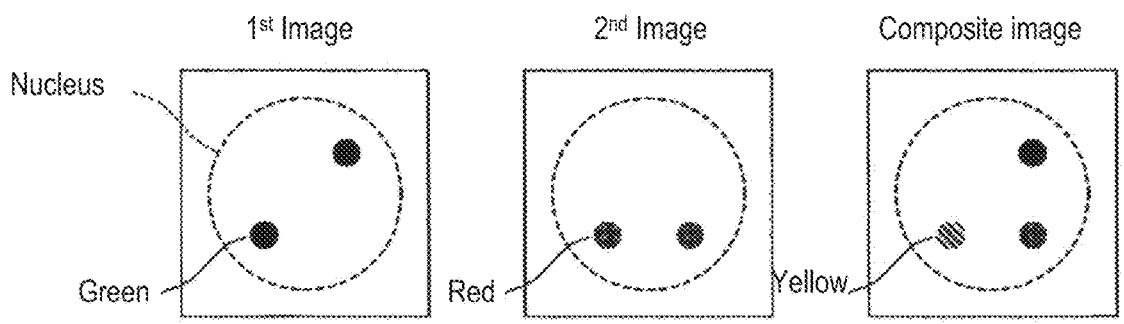
FIG. 3D Positive pattern 3

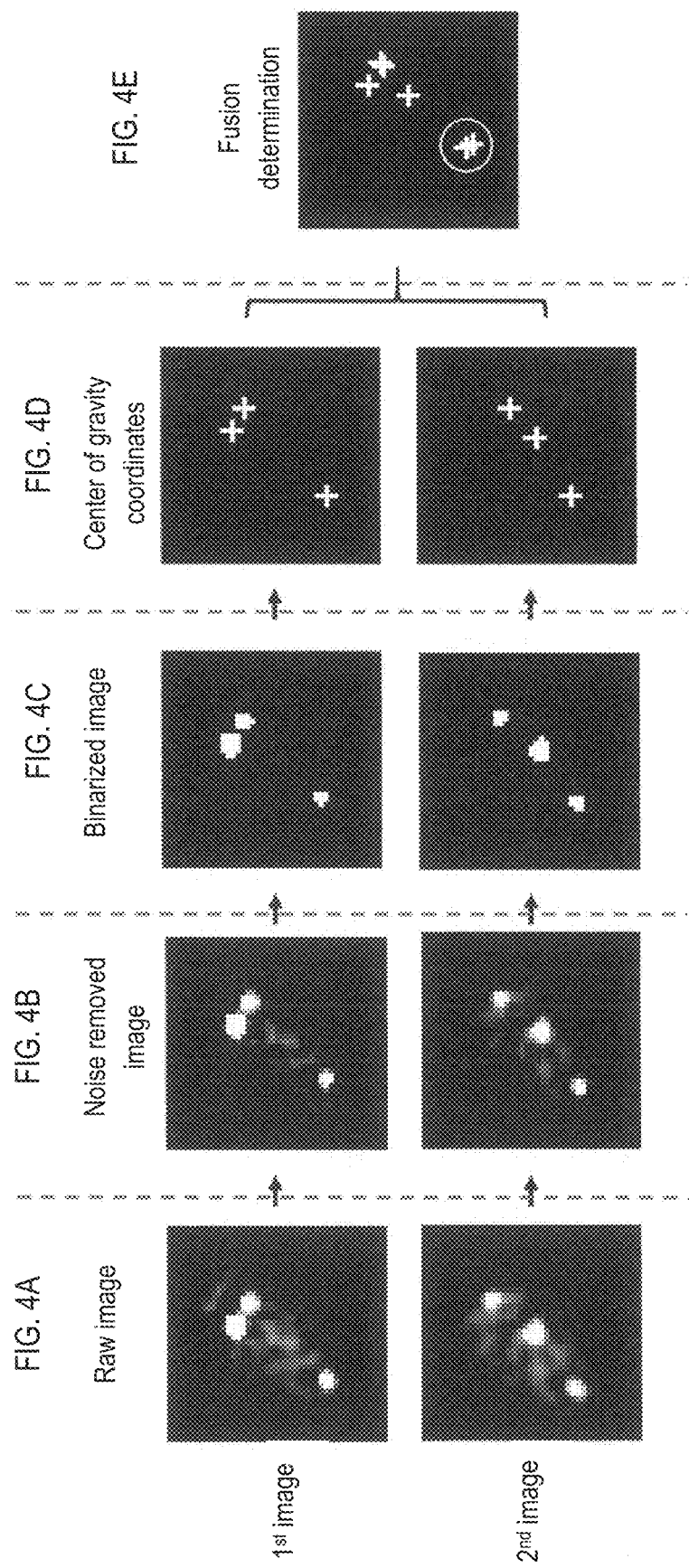

| Operator ID | Auxiliary information option settings | | | | | |
|---|---|---|---|---|---|---|
| | Ruled line | Distance between bright spots | Comparison contrast | Contour enhancement | Bright spot coordinates | |
| XXXXX | ON | ON | ON | ON | Center of gravity | |
| XXXXX | OFF | OFF | OFF | ON | Center point | |
| . | . | . | . | . | . | |
| . | . | . | . | . | . | |
| . | . | . | . | . | . | |
| . | . | . | . | . | . | |

FIG. 19

FLUORESCENCE IMAGE DISPLAY METHOD AND FLUORESCENCE IMAGE ANALYZER

RELATED APPLICATIONS

This application claims priority to Japanese Patent Application No. 2020-215595, filed on Dec. 24, 2020, the entire content of which is incorporated herein by reference.

BACKGROUND OF THE INVENTION

1. Field of the Invention

The present invention relates to a fluorescence image display method and a fluorescence image analyzer.

2. Description of the Related Art

Conventionally, a fluorescence in situ hybridization method (FISH) is known to be used in which a fluorescence-labeled probe is hybridized to the base sequence of a target site existing in the nucleus of a cell, and the fluorescence generated from the probe is measured to determine chromosomal abnormalities. Currently, analysis by the FISH method is mainly a method in which an operator visually observes fluorescently labeled cells on a slide glass using a fluorescence microscope and classifies them into normal cells and abnormal cells (hereinafter, "slide FISH method"), and in this case, a great deal of inspection labor is required, and the number of cells that can be classified is limited.

In view of this situation, an automated system for FISH inspection has been proposed (see, for example, Japanese Patent Publication No. 2018-174828. Japanese Patent Publication No. 018-174828 discloses an analyzer that acquires a fluorescence image of each cell by irradiating light on a sample containing cells having fluorescently labeled target site, and determines whether each cell is normal or abnormal by comparing the fluorescence bright spot pattern in the fluorescence image with a reference pattern corresponding to the measurement item of the sample. The analyzer of Japanese Patent Publication No. 2018-174828 determines that the two bright spots are fused when the distance between the first bright spot and the second bright spot included in the fluorescence image is less than a threshold value, and classifies these cells as abnormal cells having a fusion gene.

SUMMARY OF THE INVENTION

When determining whether two bright spots are fused bright spots, the criterion is whether the two bright spots are separated by one bright spot. Since the size, brightness, and shape of bright spots contained in a fluorescence image are not constant and change according to the state of cells and imaging conditions, there is a limit to image analysis by an automated system. Therefore, for images that cannot be analyzed by the automated system or images that the automated system determined to be abnormal cells, the operator must visually check the images and verify the analysis results by the automation system, in which case the accuracy of visual analysis is highly dependent on the skill level of the operator.

The present invention improves the accuracy of visual analysis by suppressing the influence of the skill level of the operator when the operator verifies the result of the image analysis based on the fluorescence bright spot.

In the fluorescence image display method according to the present invention, cells having target sites labeled with a fluorescent dye are imaged to obtain a fluorescence image, and the fluorescence image is analyzed by software based on the fluorescent bright spot included in the fluorescence image, then the result of the image analysis of the fluorescence image, and auxiliary information for assisting the visual analysis of the fluorescence bright spot included in the fluorescence image are displayed.

The fluorescence image analyzer according to the present invention includes a light source that irradiates light on a cell having a target site labeled with a fluorescent dye, an imaging unit that acquires a fluorescence image of the cell that emits fluorescence when the irradiated with light, a processing unit for image analysis of the fluorescence image based on the fluorescence bright spot included in the fluorescence image, and a display unit. The processing unit is configured to display a fluorescence image of the cells, the result of the image analysis, and auxiliary information assisting the visual analysis of the fluorescence bright spot included in the fluorescence image on the display unit.

According to the present invention, even an operator with a low skill level can perform highly accurate visual analysis by referring to auxiliary information.

BRIEF DESCRIPTION OF THE DRAWINGS

FIG. 3A is a diagram schematically showing an example of arrangement of fluorescent bright spots in a negative pattern, and FIGS. 3B to 3D schematically show examples of arrangements of fluorescent bright spots in positive patterns;

FIGS. 4A-4E are diagrams for demonstrating methods of image processing/analysis by a fluorescence image analyzer where FIG. 4A shows first and second raw images; FIG. 4B shows first and second noise removed images;

FIG. 4C shows first and second binarized images; FIG. 4D shows first and second center of gravity coordinates images; and FIG. 4E shows a fusion determination image;

FIG. 19 is a diagram illustrating auxiliary information option settings;

DETAILED DESCRIPTION OF THE PREFERRED EMBODIMENTS

Hereinafter, an example of the fluorescence image display method and an embodiment of the fluorescence image analyzer according to the present invention will be described in detail with reference to the drawings. The embodiments described below are merely examples, and the present invention is not limited to the following embodiments. It also is within the scope of the present disclosure to selectively combine the components of the plurality of embodiments and modifications described below.

Figure 1:
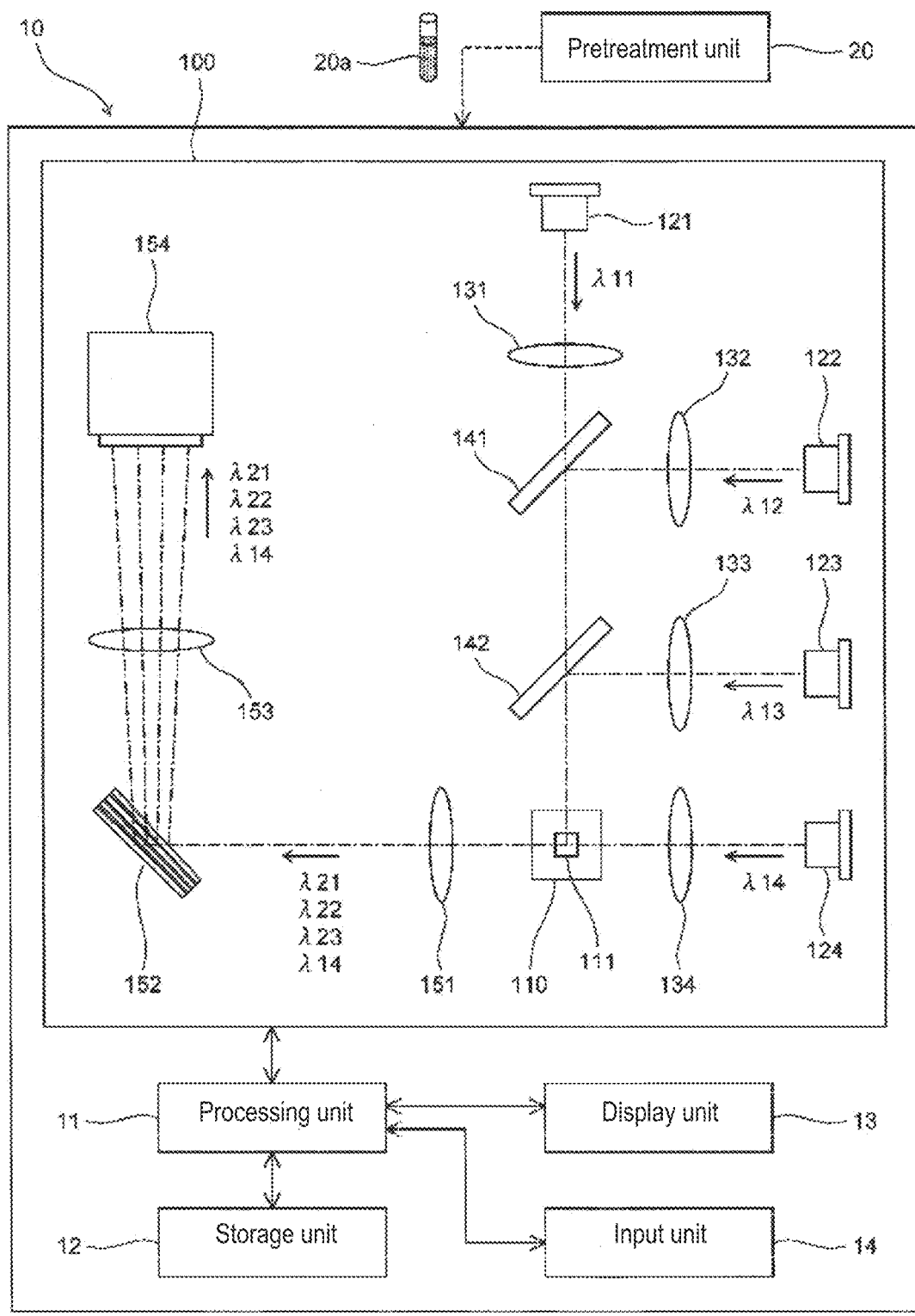
FIG. 1 is a schematic view of a fluorescence image analyzer which is an example of an embodiment.

FIG. 1 is a diagram schematically showing the structure of a fluorescence image analyzer 10 which is an example of an embodiment. As shown in FIG. 1, the fluorescence image analyzer 10 includes an imaging unit 100 that acquires a fluorescence image of cells having target sites labeled with a fluorescent dye (hereinafter, may be referred to as "fluorescence-labeled cells") for each cell, and a processing unit 11 that automatically classifies cells based on the fluorescent bright spots of the fluorescent image. The fluorescence image analyzer 10 also includes a storage unit 12, a display unit 13, and an input unit 14 connected to the processing unit 11.

As will be described in detail later, in the present embodiment the cells contained in the fluorescence image are classified into normal cells and abnormal cells by image analysis by software based on the fluorescent bright spots. In the present embodiment, a fluorescence image for which cell classification based on fluorescence bright spots by software is not possible are classified as non-targets.

The imaging unit 100 includes light sources 121 to 124 that irradiate light on fluorescently labeled cells, and an image pickup unit 154 that acquires a fluorescence image of the cells that fluoresce when irradiated with light. The imaging unit 100 includes condenser lenses 131 to 134, 151, 153, dichroic mirrors 141, 142, and an optical unit 152. In the present embodiment, the imaging unit 100 is provided with four types of light sources 121 to 124. With these four types of light sources 121 to 124, three types of fluorescence images using three types of fluorescent dyes and bright-field images of cells are acquired. Note that the bright-field image of a cell is an image obtained by detecting the light transmitted through the cell.

The fluorescence image analyzer 10 is a device that measures a sample 20a prepared by a pretreatment including a process of hybridizing a nucleic acid probe labeled with a fluorescent dye and a target site in the nucleic acid, and detects and counts abnormal cells (hereinafter referred to as "positive cells"). In this embodiment, the target sites in the nucleic acid are the BCR gene on chromosome 22 and the ABL gene on chromosome 9, and the target sites of chromosomes 9 and 22 found in chronic myelogenous leukemia cells with translocations between them are detected as positive cells based on the FISH method. That is, a cell in which the BCR gene or the ABL gene is translocated to generate the BCR-ABL fusion gene is detected as a positive cell.

The cell to be measured by the fluorescence image analyzer 10 is a white blood cell in a blood sample. The operator performs a process such as centrifugation on a blood sample collected from a subject to extract leukocytes, which are cells to be measured. In extracting leukocytes, a hemolytic agent may be used instead of centrifugation, and other blood cells may be hemolyzed to extract leukocytes. Note that the measurement target of the fluorescent image display method and the fluorescent image analyzer according to the present invention is not limited to leukocytes, and the target site is not limited to the BCR gene on chromosome 22 and the ABL gene on chromosome 9. The cell to be measured also may be a nucleated cell.

The fluorescence image analyzer 10 measures a sample 20a prepared by the pretreatment unit 20 and automatically classifies the cells contained in the sample 20a. The pretreatment unit 20 includes a mixing container for mixing the reagent and the blood sample subjected to treatment such as centrifugation, a dispensing unit for dispensing the blood sample and the reagent into the mixing container, and a heating unit or the like to heat the mixing unit. In the pretreatment unit 20, the sample 20a is prepared by performing a pretreatment including a step of labeling a target site of the cell with a fluorescent dye and a step of specifically staining the nucleus of the cell with a dye for nuclear staining. In the step of labeling the target site with the fluorescent dye, a nucleic acid probe labeled with the fluorescent dye and the target site in the nucleic acid are hybridized.

The first hybridization probe that hybridizes with the BCR gene is labeled with a first fluorescent dye that emits a first fluorescence of wavelength $\lambda 21$ when irradiated with excitation light of wavelength $\lambda 11$. By hybridizing the first nucleic acid probe and the BCR gene, the BCR gene is labeled with the first fluorescent dye. The second hybridization probe that hybridizes with the ABL gene is labeled with a second fluorescent dye that emits a second fluorescence at wavelength $\lambda 22$ when irradiated with excitation light of wavelength $\lambda 12$. By hybridizing the second nucleic acid probe with the ABL gene, the ABL gene is labeled with the second fluorescent dye. The nucleus is stained with a dye for nuclear staining that emits a third fluorescence of wavelength $\lambda 23$ when irradiated with excitation light of wavelength $\lambda 13$.

The fluorescence image analyzer 10 further includes a flow cell 110 for flowing the sample 20a prepared by the pretreatment unit 20. The flow cell 110 is made of a translucent resin or glass and has a flow path 111 for flowing the sample 20a. The flow cell 110 is provided in the imaging unit 100. In the imaging unit 100, the light sources 121 to 124 irradiate the flow cell 110 with light, and the image pickup unit 154 acquires a fluorescence image of the fluorescently labeled cells flowing from the rear side of the paper surface to the front side of the flow cell 110 in FIG. 1.

According to the FISH method using the flow cell 110 (hereinafter referred to as "flow FISH method"), a sample 20a containing fluorescently labeled cells is flowed through the flow cell 110, and a fluorescence image is acquired by imaging the cells in a fluid. Therefore, as compared with the slide FISH method, the number of cells to be analyzed can be significantly increased, and high exam accuracy can be obtained. In particular, the reproducibility is improved when the number of positive cells is small.

As described above, the imaging unit 100 is configured such that the light emitted from the light sources 121 to 124 irradiates the sample 20a flowing through the flow path 111 of the flow cell 110. An example of the light sources 121 to 123 is a semiconductor laser light source, and an example of the light source 124 is a white LED. The light source 121 is a light source for exciting the first fluorescent dye, and emits a laser beam including light having a wavelength of $\lambda 11$. The light source 122 is a light source for exciting the second fluorescent dye, and emits a laser beam including light having a wavelength of $\lambda 12$. The light source 123 is a light source for exciting a dye for nuclear dyeing, and emits a laser beam including light having a wavelength of $\lambda 13$. The light source 124 emits light for generating a bright-field image of the cell, that is, white light having a wavelength $\lambda 14$ transmitted through the cell.

The condenser lenses 131 to 134 are arranged between the light sources 121 to 124 and the flow cell 110, respectively, and collect the light emitted from the light sources 121 to 124 on the flow cell 110. The dichroic mirror 141 transmits light having a wavelength of $\lambda 11$ and reflects light having a wavelength of $\lambda 12$. The dichroic mirror 142 transmits light having wavelengths $\lambda 11$ and $\lambda 12$ and reflects light having wavelengths $\lambda 13$. By providing such an optical system, the light from the light sources 121 to 124 is applied to the flow path 111 of the flow cell 110. Then, when the sample 20a flowing through the flow path 111 is irradiated with light having wavelengths $\lambda 11$ to $\lambda 13$, the fluorescent dye labeling the cells fluoresces.

Specifically, when light having a wavelength of $\lambda 11$ is irradiated on the first fluorescent dye that labels the BCR gene, the first fluorescence having a wavelength of $\lambda 21$ is generated from the first fluorescent dye. When light of wavelength $\lambda 12$ is irradiated on the second fluorescent dye that labels the ABL gene, the second fluorescent dye produces second fluorescence of wavelength $\lambda 22$. When light having a wavelength of $\lambda 13$ is applied to a dye for nuclear dyeing that stains the nucleus, a third fluorescence having a wavelength of $\lambda 23$ is generated from the dye for nuclear dyeing. In the present embodiment, the first fluorescent color is green, the second fluorescent color is red, and the third fluorescent color is blue. Further, when the sample 20a is irradiated with the white light of the light source 124, this light passes through the cells and a bright field image is obtained.

A condenser lens 151, an optical unit 152, and a condenser lens 153 are arranged in this order between the flow cell 110 and the image pickup unit 154 along the optical path of the laser beam from the flow cell 110 side. The condenser lens 151 collects the first to third fluorescences generated from the sample 20a and the transmitted light transmitted through the sample 20a on the optical unit 152. The optical unit 152 is configured by, for example, stacking four dichroic mirrors. The four dichroic mirrors reflect the first to third fluorescences at slightly different angles and separate them on the light receiving surface of the image pickup unit 154. The condenser lens 153 collects the light reflected by the optical unit 152 on the light receiving surface of the image pickup unit 154.

The image pickup unit 154 is composed of, for example, a TDI (Time Delay Integration) camera or a CCD camera, and a TDI camera is preferably used. The image pickup unit 154 captures an image formed by the first to third fluorescence and transmitted light, hence, acquires three types of fluorescence images corresponding to the first to third fluorescences as well as a bright field image corresponding to the transmitted light, and the acquired images are transmitted to the processing unit 11. Hereinafter, the fluorescence images corresponding to the first to third fluorescence are referred to as "first image", "second image", and "third image", respectively. The processing unit 11 corrects each image by software so that the positional relationship between the subject and the pixels matches between the first to third images and the bright field image sent from the image pickup unit 154. The first to third images are preferably the same size as each other in order to analyze the overlap of bright spots.

The TDI camera configuring the image pickup unit 154 repeatedly images cells with a plurality of rows of line sensors along the direction along the flow path 111 of the flow cell 110, that is, the direction in which the sample 20a flows, and lines along the flow direction of the sample, and an image of the cell is obtained by integrating the charge of the sensors along the sample flow direction. Therefore, a high-quality cell image can be obtained without slowing down the moving speed of the sample 20a nor reducing the exposure time.

The processing unit 11 analyzes the fluorescence image acquired by the imaging unit 100 by executing the software stored in the storage unit 12, which will be described later, and automatically classifies each imaged cell as a normal cell (hereinafter referred to as "negative cell") or abnormal cell (hereinafter referred to as "positive cell"). The processing unit 11 is configured by a CPU and executes arithmetic processing related to processing/analysis of a fluorescence image. The processing unit 11 executes various processes including image analysis of the fluorescence image based on the program stored in the storage unit 12. The processing unit 11 is connected to the imaging unit 100, the storage unit 12, the display unit 13, and the input unit 14, receives signals from each device, acquires various information, and outputs control signals to each device.

The storage unit 12 is configured by a RAM, a ROM, a hard disk and the like. The storage unit 12 stores software executed by the processing unit 11 for image analysis of a fluorescence image. The display unit 13 is configured by a display that displays an automatic classification result of each cell, a fluorescence image, auxiliary information that assists visual analysis, and the like. The input unit 14 is configured by a mouse and a keyboard, and is used for inputting information such as a sample ID, switching a display screen, and selecting a fluorescence image. Note that the configurations of the storage unit 12, the display unit 13, and the input unit 14 are not particularly limited.

The processing unit 11 processes the first to third images captured by the image pickup unit 154 by executing the software stored in the storage unit 12, extracts fluorescence bright spots from the first image and the second image, respectively, and extracts the nuclear region from the third image. Then, the processing unit 11 performs analysis based on the extracted fluorescence bright spots, and classifies each cell into positive cells and negative cells. A positive cell means a cell having a chromosomal abnormality in which the BCR gene or the ABL gene is translocated, as described above. Negative cells are normal cells without chromosomal abnormalities. The processing unit 11 generates exam result information as to whether the sample 20*a* (blood sample) is positive or negative based on the result of the automatic classification performed on each cell. The processing unit 11 also causes the display unit 13 to individually display the fluorescence image for each cell.

Hereinafter, a method for extracting the fluorescence bright spots and the nuclear region will be described with reference to FIG. 2.

Figure 2A:
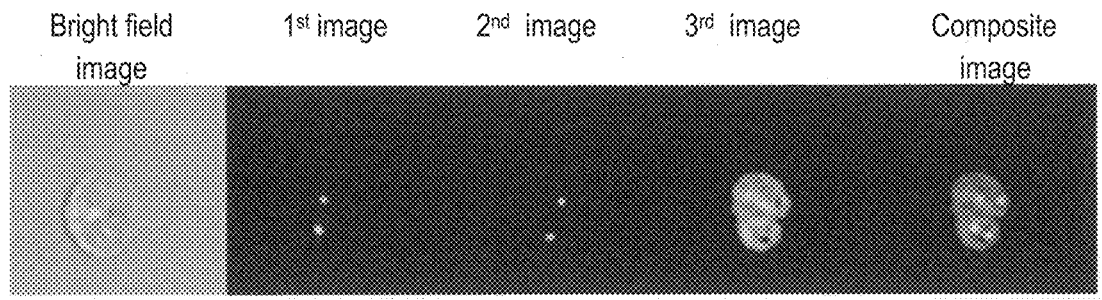
FIG. 2A is a diagram showing an example of the first to third images and bright-field images acquired by a fluorescence image analyzer.

Each image of FIG. 2A is an image obtained by imaging the white blood cells after pretreatment by the flow FISH method; the color tone of the first to third images and the composite image of FIG. 2A are changed to gray after the gradation is inverted. The third image of FIG. 2B, the first image of FIG. 2C, and the second image of FIG. 2D are schematically shown images obtained from the same region of the sample 20*a* flowing through the flow cell 110. Note that in the present embodiment the fluorescence bright spot is a spot of fluorescence emitted by the fluorescent dye of the nucleic acid probe, and is a region in which the brightness (pixel value) of each pixel comprising the image is higher than the brightness of the surrounding pixels. The fluorescence bright spot is extracted by a binarization treatment described later.

In the example shown in FIG. 2A, the first image has two bright spots of the first fluorescence having a wavelength of λ21, and the second image has two bright spots of the second fluorescence having a wavelength of λ22. The third image is a fluorescence image corresponding to the third fluorescence of wavelength λ23 indicating the region of the nucleus. The composite image is an image in which the first to third images are superimposed, and there are two bright spots of the first fluorescence and two bright spots of the second fluorescence in the nuclear region of the composite image, for a total of four bright spots. In the bright field image, the actual shape of the cell can be confirmed. Since, in the flow path 111 of the flow cell 110, the sample 20*a* flows in a state in which the cells are separated from each other, and when this is imaged by the image pickup unit 154, as shown in FIG. 2A, a fluorescence image and a bright-field image are acquired for each cell.

Figure 2B:
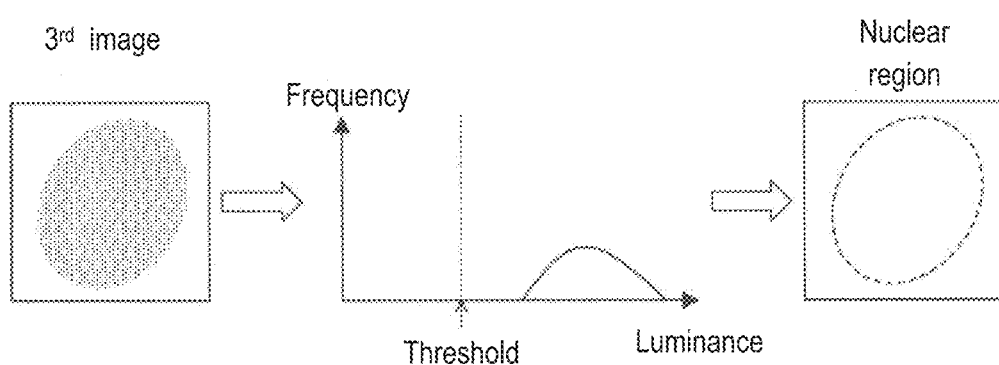
FIG. 2B demonstrates a method of extracting a nuclear region performed by the fluorescence image analyzer.

When the third image shown in FIG. 2B is acquired, the processing unit 11 creates a graph of the brightness and frequency as shown in the center of FIG. 2B based on the brightness of each pixel on the third image. The frequency on the vertical axis indicates the number of pixels. The processing unit 11 sets a brightness threshold value as a boundary between the fluorescence bright spot and the background based on the Otsu method. Then, the processing unit 11 performs a binarization process representing the third image by the pixels having the brightness below the threshold value and the pixels having the brightness above the threshold value, and extracts the range in which the pixels having the brightness higher than the threshold value are distributed. Note that in the third image, when two nuclei overlap, the cell is excluded from the classification target.

Figure 2C:
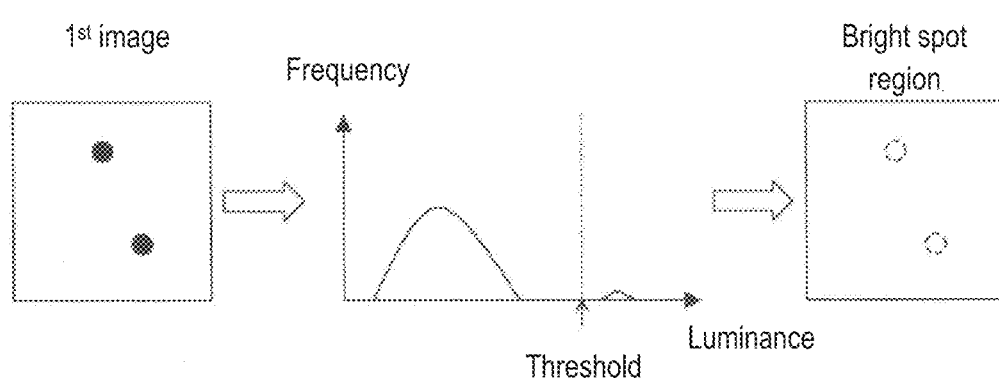
FIG. 2C demonstrates the extraction method of the first image fluorescence bright spot performed by the fluorescence image analyzer.
Figure 2D:
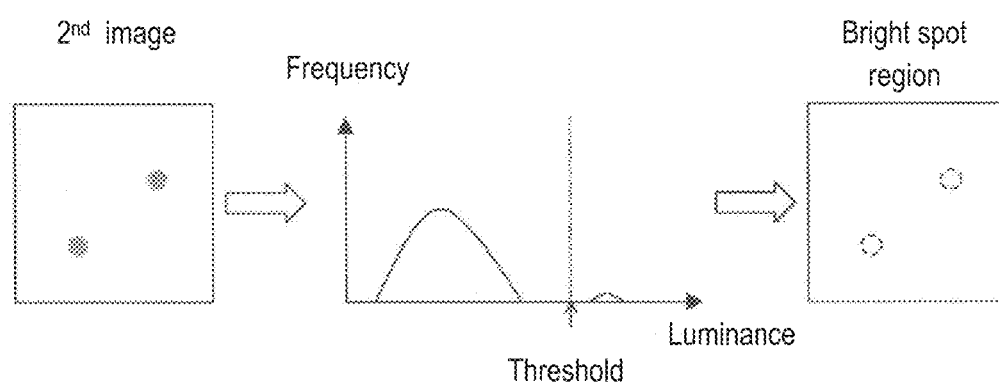
FIG. 2D demonstrates the extraction method of the second image fluorescence bright spot performed by the fluorescence image analyzer

When the first image shown in FIG. 2C is acquired, the processing unit 11 creates a graph of the brightness and frequency as shown in the center of FIG. 2C based on the brightness of each pixel on the first image. Similar to the processing of the third image, the processing unit 11 sets a brightness threshold value in this graph, and extracts a range in which pixels having a brightness larger than the threshold value are distributed as a region of the fluorescence bright spot. Note that when the fluorescence bright spot extracted from the first image exists at a position outside the nuclear region, the cell is excluded from the classification target.

When the second image shown in FIG. 2D is acquired, similar to the case of the first image, the processing unit 11 creates a graph of brightness and frequency as shown in the center of FIG. 2D based on the brightness of each pixel on the two images. In this graph, the processing unit 11 sets a brightness threshold value, and extracts a range in which pixels having a brightness larger than the threshold value are distributed as a region of fluorescence bright spots. Note that when the fluorescence bright spot extracted from the second image exists at a position outside the nuclear region, the cell is excluded from the classification target.

The processing unit 11 also may extract the nuclear region from the third image by calculation according to the above procedure without creating the graphs shown in FIGS. 2B to 2D, and extract the region of the fluorescence bright spots from the first image and the second image. Although the processing unit 11 may extract the nuclear region from the third image, the nuclear region also may be detected based on the bright field image. In that case, it is possible to omit the acquisition of the third image.

Next, the automatic classification of cells based on the bright spot pattern by the processing unit 11 will be described with reference to FIG. 3.

FIG. 3A shows an example of arrangement of fluorescence bright spots of negative cells without chromosomal abnormalities, that is, negative patterns, and FIGS. 3B to 3D show arrangement of fluorescence bright spots of positive cells with chromosomal abnormalities, that is, positive patterns. The first image and the second image of FIG. 3 are superposed images of a third image showing a nuclear region, and the composite image means an image in which the first to third images are superposed. The fluorescence image of the present embodiment includes a first image, a second image, a third image, and a composite image. Hereinafter, the bright spot of the first fluorescence constituting the first image is referred to as a "first bright spot", and the bright spot of the second fluorescence constituting the second image is referred to as a "second bright spot".

FIG. 3 illustrates the alphabet of "GRF" and the numbers "0 to 3" as the pattern of fluorescence bright spots. The "G" of the fluorescence bright spot pattern indicates the green first bright spot in the composite image, and the "R" indicates the red second bright spot in the composite image. The "F" indicates a yellow fusion bright spot in the composite image. The numbers immediately following G, R, and F indicate the number of bright spots of G, R, and F included in the composite image, respectively.

For example, in the case of the negative pattern "G2R2F0" shown in FIG. 3A, there are two first bright spots in the first image, two second bright spots in the second image, and zero fusion bright spots in the composite image. Similarly, in the case of the positive pattern "G2R3F1" in FIG. 3B, there are two first bright spots in the first image, three second bright spots in the second image, and one fusion bright spot in the composite image.

As shown in FIG. 3A, when there is no chromosomal abnormality such as translocation of BCR locus and ABL locus, each gene exists independently as one pair in one nucleus. Therefore, the first image has two first bright spots in one nuclear region, and the second image has two second bright spots in the nuclear region. Then, when the first image and the second image captured in the same size are superimposed and combined, the two first bright spots and the two second bright spots are contained in one nuclear region without overlap in the composite image. The pattern of fluorescence bright spots in which the first bright spot and the second bright spot do not overlap each other in the nuclear region as shown in FIG. 3A is a negative pattern in which no chromosomal abnormality is observed.

As shown in FIG. 3B, when a part of the ABL gene is transferred to chromosome 22 due to translocation, the first image has two first bright spots in the nucleus and the second image has three second bright spots in the nucleus. In this case, when the first image and the second image are combined, in the composite image, two first bright spots, one second bright spot, and one fusion bright spot in which the first bright spot and the second bright spot mutually overlap are present in one nucleus. The pattern of fluorescent bright spots as shown in FIG. 3B is a positive pattern in which a chromosomal abnormality is observed.

The fusion bright spot generated by overlapping the first bright spot and the second bright spot appears yellow in the composite image. The presence or absence of fusion bright spots, along with the number of fluorescence bright spots is an important classification index in FISH inspection.

As shown in FIG. 3C, when a part of the BCR gene is moved to chromosome 9 and a part of the ABL gene is moved to chromosome 22 due to the translocation, there are three first bright spots in the nucleus of the first image, and three second bright spots in the nucleus of the second image. In this case, when the first image and the second image are combined, in the composite image, one first bright spot, one second bright spot, and two fusion bright spots configured by mutually overlapping first bright spots and second bright spots will exist in one nucleus. The pattern of fluorescence bright spots as shown in FIG. 3C is a positive pattern in which chromosomal abnormalities are observed.

As shown in FIG. 3D, when all of the ABL gene has been transferred to chromosome 22 by translocation, two first bright spots exist in the nucleus in the first image, and two second bright spots exist in the nucleus in the second image. In this case, when the first image and the second image are combined, in the composite image, one first bright spot, one second bright spot, and a fusion bright spot configured by a first bright spot and a second bright spot overlapping each other will exist in one nucleus. The pattern of fluorescence bright spots as shown in FIG. 3D is a positive pattern in which a chromosomal abnormality is observed.

According to the FISH method described above, it is possible to determine whether each cell is positive with a chromosomal abnormality based on the number of each of the red and green fluorescence bright spots and the number of fusion bright spots in the composite image of the first image and the second image. The processing unit 11 counts the number of first bright spots in the first image of each cell, the number of second bright spots in the second image, and the number of fusion bright spots of mutually overlapping first bright spot and second bright spot when the first image and the second image are combined. Based on the counted number of first bright spots (G), the number of second bright spots (R), and the number of fusion bright spots (F), the processing unit 11 determines that a cell is positive or negative by classifying cells as shown in FIG. 3A to FIG. 3D.

The storage unit 12 stores a negative pattern "G2R2F0" illustrated in FIG. 3A and positive patterns "G2R3F1", "G3R3F2" and "G2R2F1" illustrated in FIGS. 3B to 3D, as well as multiple bright spot patterns. The processing unit 11 determines whether a cell is positive or negative by comparing the negative pattern and the positive pattern stored in the storage unit 12 with the bright spot pattern obtained by counting the bright spots included in the fluorescence image of the cell to be analyzed.

Hereinafter, a method of extracting bright spots and determining fusion bright spots by the processing unit 11 will be described with reference to FIGS. 4 and 5.

FIG. 4A shows a first image and a second image obtained by the imaging unit 154. As shown in FIG. 4B, the processing unit 11 removes noise from the fluorescence images (first image and second image). Since noise is generally present in a fluorescence image, the processing unit 11 executes noise removal processing using, for example, a noise removing means such as a top hat filter.

The processing unit 11 performs binarization processing on the noise-removed fluorescence image as shown in FIG. 4C. The setting of the threshold value in the binarization process is as described above. As shown in FIG. 4D, the processing unit 11 calculates the coordinates of the center of gravity of the fluorescence bright spots extracted by the binarization process. The center of gravity coordinates mean the coordinates of the geometric center of gravity of the fluorescence bright spot, and can be calculated based on a predetermined formula or the like. As shown in FIG. 4E, the processing unit 11 determines whether the first and second bright spots that are close to each other are fusion bright spots from the distance D between the centers of gravity of the first bright spot and the second bright spot. The first bright spot and the second bright spot existing in the circle drawn in the composite image of FIG. 4E are mutually proximate, and there is a possibility of a fusion bright spot generated due to the translocation of the BCR gene or the ABL gene.

Figure 5:
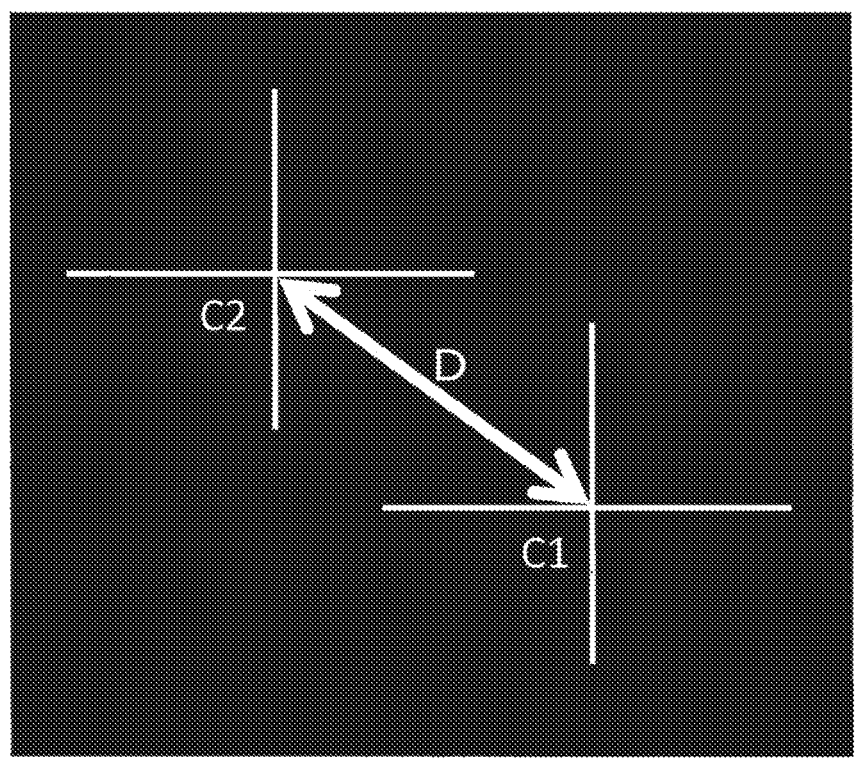
FIG. 5 is a diagram for demonstrating a method of image processing/analysis by a fluorescence image analyzer.

FIG. 5 is a schematic diagram for describing the fusion determination of FIG. 4E in detail. As shown in FIG. 5, the processing unit 11 calculates the distance D between the center of gravity coordinates C1 of the first bright spot and the center of gravity coordinates C2 of the second bright spot, and compares the distance D between the centers of gravity with a predetermined threshold value. As a predetermined threshold value, a distance corresponding to the diameter of one standard fluorescence bright spot is used. A fixed value is used for the threshold value regardless of the sample. Note that the threshold value may not be a fixed value, and the threshold value may be set variably depending on the sample. For example, a representative value thereof may be calculated from the diameters of a plurality of fluorescence bright spots extracted from a plurality of cells contained in a sample 20a, and the representative value may be applied to the threshold value. The representative value also may be an average value, a median value, or a mode value.

When the distance D between the centers of gravity is equal to or less than the threshold value, the processing unit 11 determines that the first bright spot and the second bright spot are fused. When the distance D between the centers of gravity is larger than the threshold value, the processing unit 11 determines that the first bright spot and the second bright spot are not fused. The processing unit 11 calculates the distance D between the centers of gravity of all the first bright spots existing in the nuclear region from each of the second bright spots, and compares them with the threshold values to make a fusion determination. The processing unit 11 counts the number of fusion bright spots for each cell. Note that although, in FIG. 4E and FIG. 5, the fusion determination is performed on the composite image of the first image and the second image as described above for simplicity of explanation, for the fusion determination performed by the processing unit 11, it is sufficient if the distance between the coordinates of the center of gravity of each bright point in the first image and the coordinates of the center of gravity of each bright point in the second image is obtained, and it is not essential to create a composite image.

The fusion determination of whether the first bright point and the second bright point overlap also may be performed by using the distance between the center point of the first bright point and the center point of the second bright point instead of the distance D between the centers of gravity. In the present specification, the center point means the point having the highest brightness among the fluorescence bright spots and the pixel having the highest brightness. When the distance between the center points of the first bright spot and the second bright spot is equal to or less than a predetermined threshold value, the processing unit 11 may determine that the first bright spot and the second bright spot are fused, and when the distance between the center points is larger than a predetermined threshold value, it may be determined that the bright spots are not fused.

Further, it is also possible to make the fusion determination by comparing the ratio of the regions where the first bright spot and the second bright spot overlap each other, that is, the ratio of the pixels configuring the first bright spot at the same position (same coordinates) as the pixels configuring the second bright spot with the threshold value.

Figure 6:
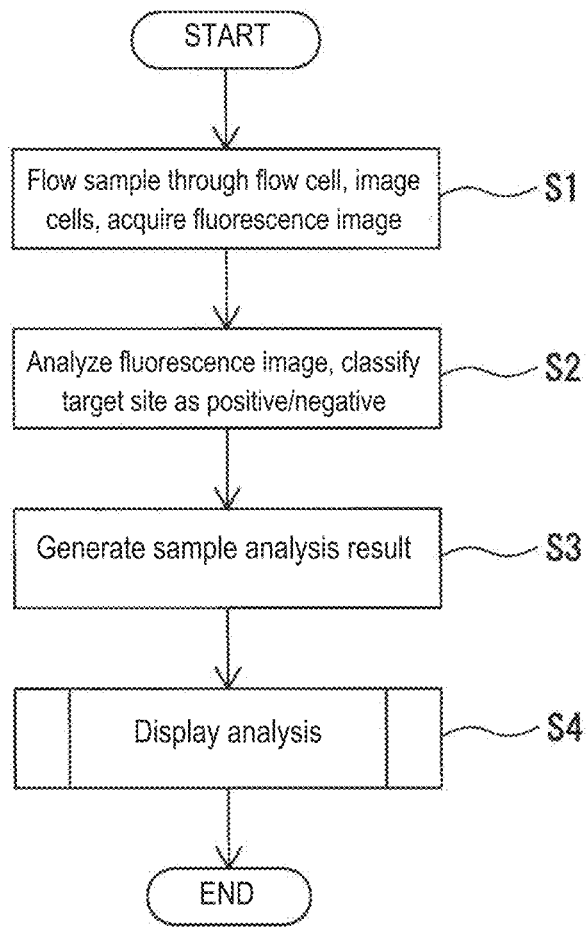
FIG. 6 is a flowchart showing an example of an analysis process by a fluorescence image analyzer.

FIG. 6 is a flowchart showing an example of the analysis process by the fluorescence image analyzer 10. When the processor of the processing unit 11 executes the program stored in the storage unit 12, the processing shown in FIG. 6 is executed. When the operator sets sample 20a obtained by performing pretreatment using the pretreatment unit 20 in the fluorescence image analyzer 10 and an instruction to start measurement is given via the input unit 14, the processing unit 11 starts a series of analysis processes.

In step S1, the processing unit 11 controls the fluid circuit of the fluorescence image analyzer 10 to flow the sample 20a into the flow cell 110. The processing unit 11 causes the light sources 121 to 124 to emit light. In this way the cells in the sample 20a flowing through the flow cell 110 are irradiated with light. The processing unit 11 causes the imaging unit 154 to capture a fluorescence image and a bright-field image of the cells. In this way a fluorescence image and a bright-field image are acquired for each cell. As the fluorescence image, a first image corresponding to the first fluorescence, a second image corresponding to the second fluorescence, and a third image corresponding to the third fluorescence are acquired. The fluorescence image and the bright field image for each cell are stored in the storage unit 12.

In step S2, the processing unit 11 analyzes the fluorescence images (first to third images) by software, and classifies the cells in the fluorescence images into positive cells (Positive) and negative cells (Negative). The processing unit 11 also classifies fluorescence images that do not satisfy the predetermined conditions for cell classification by software into excluded images (Excluded). Specifically, as described with reference to FIG. 4, the processing unit 11 removes noise from the captured image and performs binarization processing to extract fluorescence bright spots and nuclear regions. As the fluorescence bright spots, the first bright spot is extracted from the binarized first image, and the second bright spot is extracted from the second image. The processing unit 11 determines the coordinates of the center of gravity of each bright spot, as described with reference to FIGS. 4 and 5.

The processing unit 11 counts the number of first bright spots included in the composite image, the number of second bright spots included in the composite image, and the number of fusion bright spots included in the composite image based on the coordinates of the center of gravity of each bright spot. Next, the processing unit 11 classifies each cell into a negative cell or a positive cell as described with reference to FIG. 3 based on the number of bright spots counted and the negative pattern and the positive pattern. The processing unit 11 also classifies a fluorescence image whose shape, size, and brightness of the fluorescence bright spot do not satisfy a predetermined condition as a non-target image. Hereinafter, a specific example of the non-target classification by the processing unit 11 will be described.

When the shape of the fluorescence bright spot diverges from a perfect circle such as an elliptical shape, the processing unit 11 determines that the fluorescence image is not subject to classification by software, and classifies the fluorescence image as non-target. The first bright spot and the second bright spot usually have a shape near to a perfect circle, but may have a shape distant from a perfect circle such as an elliptical shape. This is because the moving speed of cells flowing through the flow path 111 of the flow cell 110 and the charge transfer speed of the line sensor of the TDI camera do not match, and the fluorescence bright spot extends or shrinks in the Y direction, which is the direction of the sample flow. In this case, it is difficult to obtain accurate coordinates of the center of gravity of the fluorescence bright spot, and software may make an erroneous fusion determination, hence, such a fluorescence image is excluded from cell classification.

For example, when the ratio (Y/X) of the length of the fluorescence bright spot in the Y direction to the length in the X direction orthogonal to the Y direction exceeds a predetermined threshold value, the processing unit 11 classifies these cells as non-target cells. Note that instead of the length ratio (Y/X), another index indicating the shape of the fluorescence bright spot, such as the circularity of the fluorescence bright spot may be used.

When the size of the fluorescence bright spot exceeds a predetermined threshold value, the processing unit 11 excludes the fluorescence image from the classification by software, and classifies the fluorescence image into the non-target category. The first bright spot and the second bright spot are usually about the same size, but only a part of the fluorescence bright spots may be imaged in a large size. The cause of this is that there are fluorescently labeled sites of cells separated in the depth direction along the optical axis of the TDI camera. In this case, it is difficult to obtain accurate coordinates of the center of gravity of the fluorescence bright spot, and software may make an erroneous fusion determination, hence, such a fluorescence image is excluded from cell classification. For example, when the area of the fluorescence bright spot exceeds a predetermined threshold value, the processing unit 11 classifies the fluorescence image as a non-target.

When the brightness of the fluorescence bright spot is lower than a predetermined threshold value, the processing unit 11 excludes the fluorescence image from the classification by software, and classifies the fluorescence image as non-target. The maximum brightness value in each of the first image and the second image is usually about the same, but it is considered that the brightness is greatly reduced due to the influence of preprocessing and the like. Although the sample 20a is prepared by a pretreatment that fluorescently labels the target site of the cells, it is generally difficult to perform a homogeneous pretreatment on all cells, hence staining that is not fluorescently labeled to the target level may develop. For example, when at least one of the maximum value of the brightness value of the first image and the maximum value of the bright spot of the second image is less than a predetermined threshold value, the processing unit 11 classifies the fluorescence image as a non-target.

Next, in step S3, the processing unit 11 generates an analysis result of the sample 20a based on the result of classifying the cells. Specifically, the processing unit 11 counts the number of positive cells, the number of negative cells, and the number of fluorescence images determined to be excluded from the target, respectively. The processing unit 11 generates an analysis result of the sample 20a based on the counting result.

In step S4, the processing unit 11 causes the display unit 13 to display the analysis result screen.

Hereinafter, the display screen of the fluorescence image analyzer 10 showing the analysis result of the sample 20a will be described with reference to FIG. 7.

Figure 7:
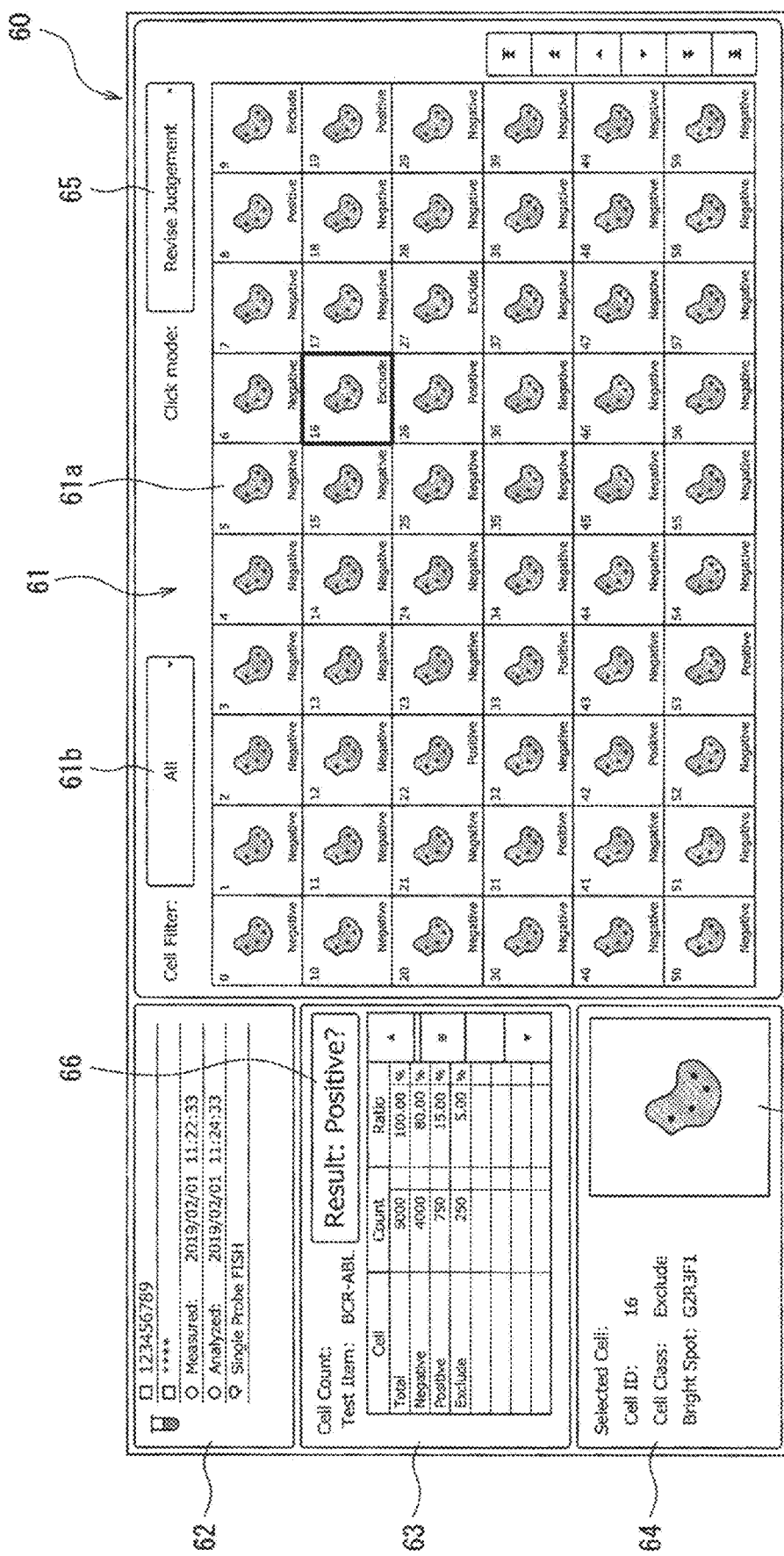
FIG. 7 is a diagram showing an example of a display screen of a fluorescence image analyzer.

FIG. 7 is a diagram showing a screen 60 showing the analysis result of the sample 20a (the sample used for preparing the sample 20a). As shown in FIG. 7, the screen 60 displays sample identification information such as a sample ID, the number/ratio of cells for each pattern of fluorescence bright spots, and the number/ratio of positive cells and negative cells. On the screen 60, a test result indicating whether the sample 20a containing these cells is positive or negative is also displayed in the test result display field 66. A doctor or the like can determine whether the sample 20a is positive or negative by referring to the display content on the screen 60.

The processing unit 11 performs the above-mentioned image analysis on all the fluorescence images acquired by the imaging unit 154, and then displays the screen 60 on the display unit 13. Note that it is not always necessary to wait for the display of the screen 60 until the analysis of all the fluorescence images is completed, inasmuch as the screen 60 including the fluorescence image for which the analysis has been completed and the image analysis result may be displayed during the analysis of the fluorescence image. The image analysis result (result of automatic cell classification and classification result of non-target images) is stored in the storage unit 12 together with identification information such as a sample ID. The operator can read the analysis result of the target sample from the storage unit 12 and check the screen 60.

On the screen 60, thumbnails of fluorescence images for each cell are displayed. The fluorescence image displayed as a thumbnail is a composite image in which the first to third images are combined. In addition to the image display field 61 for individually displaying a plurality of composite images, the screen 60 is provided with a basic information field 62, an analysis result field 63, a selected image display field 64, and an exam result display field 66. The screen 60 also is provided with an operation unit 65 for correcting the result of automatic classification.

In the basic information field 62, information such as identification information of the sample 20a, measurement date and time, analysis date and time, and measurement method are displayed. In the analysis result field 63, the number and ratio of positive cells, negative cells, and non-target cells are displayed. In the example shown in FIG. 7, the fluorescence image of the positive cell, the fluorescent image of the negative cell, and the fluorescent image of the non-target cell are indicated by the characters "Positive", "Negative", and "Exclude", respectively. In the analysis result field 63, the number and ratio of cells for each fluorescence bright spot pattern displayed on the screen 60 may be displayed. In the selected image display field 64, an enlarged image 641 of the fluorescence image displayed as a thumbnail in the image display field 61 is displayed. In the test result display field 66, the test result of the sample based on the number of positive cells and the number of negative cells is displayed. If the ratio of the number of positive cells to the total number of measured cells exceeds a predetermined threshold, the test result of the sample is positive. In the example of FIG. 7, as shown in the analysis result field 63, the total number of cells (Total) is 5000, the number of positive cells is 750, and the ratio of positive cells to the whole is 15%. In the example of FIG. 7, the proportion of positive cells exceeds the threshold value, and "Positive?", Which indicates positive as the test result of the sample, is displayed in the test result display field 66.

In the selected image display field 64, the cell ID (Cell ID) of the selected fluorescent image, the cell classification (Cell Class) which is the result of image analysis on the fluorescent image, and the bright spot pattern (Bright Spot) are displayed. In the selected image display field 64, the alphabet of "GRF" and the numbers "0 to 3" are displayed as the pattern of the fluorescence bright spots. The "G" of the fluorescence bright spot pattern indicates the green first bright spot in the composite image, and the "R" indicates the red second bright spot in the composite image. The "F" indicates a yellow fusion bright spot in the composite image. The number following each of the GRFs indicates the number of each bright spot.

The image display field 61 is provided with a plurality of display cells 61a and a filter operation unit 61b. A plurality of display cells 61a are arranged vertically and horizontally on the screen 60. The composite images are individually displayed one by one in the display cell 61a, and the cell identification information (cell ID) and the cell/fluorescence image classification result (positive/negative/non-target) as the image analysis result are displayed. In the image display field 61, for example, by clicking one display cell 61a, the fluorescence image displayed in the display cell 61a can be selected. When one image is selected, the display cell 61a is highlighted, for example, the display mode of the frame of the display cell 61a changes. In the display cell 61a, a composite image of cells belonging to the classification displayed on the filter operation unit 61b is displayed.

The filter operation unit 61b is configured so that the display target can be selected by, for example, a pull-down method, and also functions as an operation unit for switching the image in the image display field 61. In the present embodiment, the options of the filter operation unit 61b include a first option of displaying the composite images of all the analyzed cells in the order of imaging or randomly, a second option of displaying only the positive cell images, a third option for displaying only the negative cell images, and a fourth option for displaying only the non-target images. In the example shown in FIG. 7, the first option "All" is selected.

For example, when one image in the image display field 61 is selected, the processing unit 11 displays the image in the selected image display field 64. The image in the selected image display field 64 is an enlarged image 641 that is displayed in a larger size than the image in the display cell 61a. In the selected image display field 64, cell identification information (cell ID), cell/fluorescence image classification result (positive/negative/non-target), which is an image analysis result, and fluorescence bright spot pattern are displayed as information regarding the selected image.

The operation unit 65 is an operation unit for correcting the classification of each automatically classified cell, and is operated by an operator. The operation unit 65 is configured by, for example, a pull-down method. In the present embodiment, the options of the operation unit 65 include three options of positive, negative, and non-target. Alternatively, the operation unit 65 may have two options, positive and negative. The modification of the cell/fluorescence image classification by the operation of the operation unit 65 is performed on the image selected in the image display field 61, that is, the enlarged image 641 displayed in the selected image display field 64.

Hereinafter, auxiliary information that assists the visual analysis of cells will be described with reference to FIG. 8. Auxiliary information is information that assists in determining the presence or absence of a fusion bright spot based on a fluorescence bright spot, and includes information visually added to a fluorescence image of a cell, information on the quality of the fluorescence image, or a fluorescence image of a cell.

Figure 8:
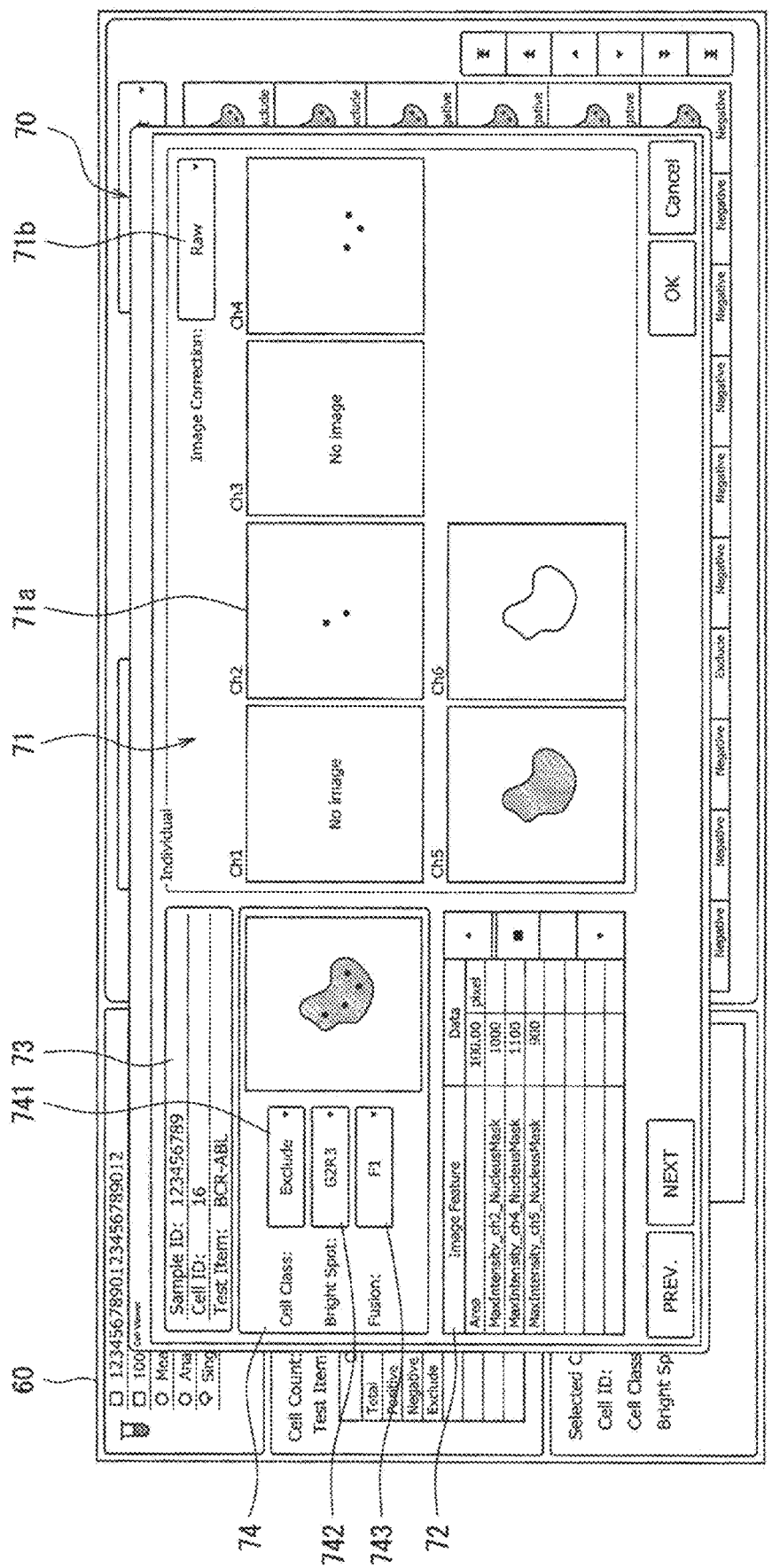
FIG. 8 is a diagram showing a display example of auxiliary information.

FIG. 8 is a diagram showing a pop-up display unit 70 displayed when an arbitrary display cell 61*a* is double-clicked on the screen 60. As shown in FIG. 8, the pop-up display unit 70 is overlaid on the screen 60 and includes auxiliary information fields 71 and 72 for assisting the visual analysis of cells.

Similar to the screen 60, the pop-up display unit 70 is provided with a basic information field 73 and an analysis result field 74. In the basic information field 73, for example, sample identification information, cell identification information, measurement items, and the like are displayed. The analysis result field 74 is a part showing the result of automatic classification by the processing unit 11. In the analysis result field 74, a cell classification field 741, a bright spot number field 742, and a fusion bright spot number field 743 are displayed. The result of automatic cell classification is displayed in the cell classification field 741. In the example of FIG. 8, "Positive" indicating that the cells are positive is displayed. The number of bright spots field 742 displays the number of first bright spots and the number of second bright spots. In the example of FIG. 8, "G2R3" indicating that the number of the first bright spots (G) is 2 and the number of the second bright spots (R) is 3 is displayed. The number of fusion bright spots 743 indicates the number of fusion bright spots. In the example of FIG. 8, "F1" indicating that the number of fusion bright spots is one is displayed. Each field 741 to 743 is composed of a pull-down menu, and the operator can correct the classification result by operating the pull-down menu based on the result of the visual analysis. In the analysis result field 74, for example, the classification result (positive, negative, or not applicable) of the cell/fluorescence image by image analysis, the number of first and second bright spots, the number of fusion bright spots, and the like are displayed. In the analysis result field 74, the same composite image as that displayed in the image display field 61 is also displayed.

In the present embodiment, each display unit of the analysis result field 74 is configured as an operation unit capable of modifying the result of automatic classification. Although the screen 60 is also provided with an operation unit 65 for correction, usability is improved by providing a correction function in the pop-up display unit 70 including the auxiliary information fields 71 and 72. The operator can correct the classification of the fluorescence image from non-target to positive cells or negative cells by the correction function of the analysis result field 74. As illustrated in FIG. 8, when the number of fluorescence bright spot patterns and fusion bright spots is displayed in the analysis result field 74, these are also configured to be correctable according to the correction of the classification. Note that the correction function may be provided in the pop-up display unit 70, and is not limited to the pull-down method of the analysis result field 74.

The processing unit 11 displays the pop-up display unit 70 for the fluorescence image selected by the operator. The processing unit 11 displays the pop-up display unit 70 when the operator double-clicks the display cell 61*a* in the image display field 61 of the screen 60. The operation for displaying the pop-up display unit 70 is not limited to double-clicking, and the pop-up display unit 70 can be displayed when a predetermined operation is performed. The predetermined operation may be, for example, pressing a predetermined key (for example, the Enter key) of the keyboard when an arbitrary display cell 61*a* is selected, clicking the display cell 61*a* on the display unit 60 and dragging the display cell 61*a* out of the window, or pressing and holding the display cell 61*a*. In another example, in a form in which a call button for calling the pop-up screen 70 is arranged on the screen 60, the predetermined operation may be to operate the call button.

Note that the image selection operation by the operator is not limited to double-clicking the display cell 61*a*. The screen 60 may be provided with, for example, an input unit capable of inputting an identification number of a cell for displaying the pop-up display unit 70. In this case, the processing unit 11 displays the pop-up display unit 70 for the cell image of the input number. Alternatively, the pop-up display unit 70 may be displayed by manipulating the image in the selected image display field 64.

The auxiliary information field 71 displays, as auxiliary information, a plurality of segment images obtained by dividing a composite image of cells selected by the operator into a plurality of monochromatic images. The segment image is a first image showing the first bright spot, a second image showing the second bright spot, and a third image showing the nuclear region. As described above, the composite image individually displayed in the image display field 61 is configured by superimposing three segment images of the first to third images. Displaying this composite image by dividing it into a plurality of segment images makes it possible to confirm, for example, the number, position, size, shape and the like of fluorescence bright spots in each segment image, such that useful information for visual analysis is obtained.

The auxiliary information field 71 is provided with a plurality of display areas 71*a* capable of displaying a plurality of segment images. In the example shown in FIG. 8, six display areas 71*a* are provided, wherein three images are displayed such that the first image is in the display area 71*a* of channel 2, the second image is in the display area 71*a* of channel 4, and the second image is in the display area 71*a* of channel 5. The first image has two fluorescence bright spots, and the second image has three fluorescence bright spots. A bright field image is displayed in the display area 71*a* of the channel 6. In the present embodiment, four display areas 71*a* are used, but for example, more display areas 71*a* may be used depending on the measurement item.

The plurality of display areas 71*a* have the same size as each other. When the first to third images of the auxiliary information field 71 have the same size as each other and the display areas 71*a* (channels 2, 4, 5) are overlapped with each other, the composite image shown in the analysis result field 74 can be displayed in a positional relationship. The images in each display area 71*a* may be enlarged or reduced in conjunction with each other at the same magnification. Alternatively, the image of each display area 71*a* may be individually enlarged or reduced.

The auxiliary information field 71 is provided with an image type display unit 71b that displays the type of image being displayed in the display area 71a. The image type display unit 71b also functions as an operation unit that enables switching of images. The image type display unit 71b is configured so that a display target can be selected by, for example, a pull-down method. In the present embodiment, as options of the image type display unit 71b, that is, as the type of the image displayed in the display area 71a, an image captured before image processing, an image after noise removal, a binarized image, and a center of gravity coordinate map are possible. In the example shown in FIG. 8, the captured image "Raw" before image processing is selected. By operating the image type display unit 71b, it is possible to display the captured image before image processing, the image after noise removal, and the binarized image as auxiliary information.

Figure 9:
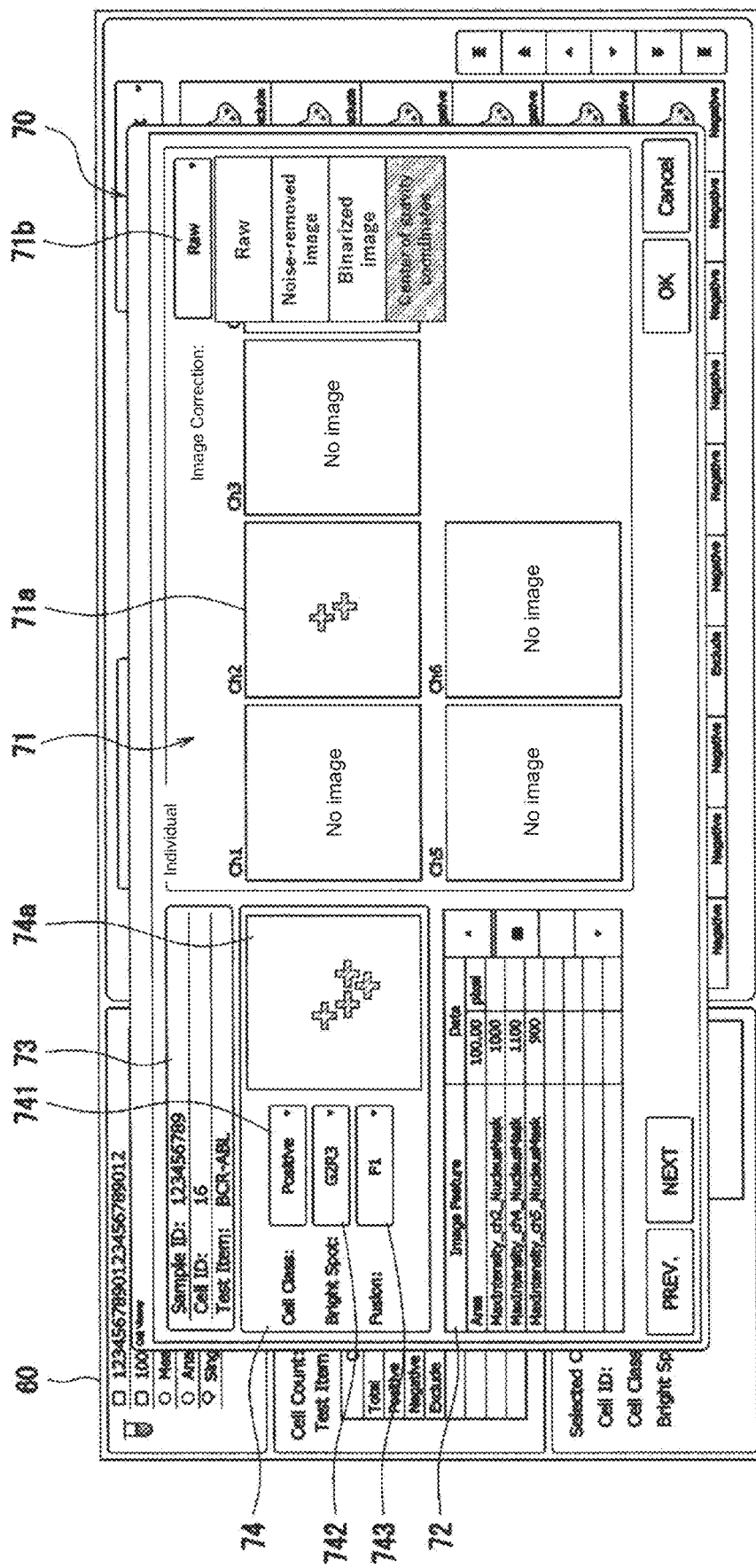
FIG. 9 is a diagram showing another display example of auxiliary information.

FIG. 9 illustrates a state in which the pull-down menu is displayed by operating the image type display unit 71b. As shown in FIG. 9, when the image type display unit 71b is operated, (1) "Raw", (2) "Noise-removed image", (3) "Binarized image", and (4) "Center of gravity" can be selected. "Raw" is an option for displaying the captured image before image processing. "Noise-removed image" is an option for displaying the image after noise removal.

"Binarized image" is an option for displaying the binarized image. The "Center of gravity coordinates" is an option for displaying the center of gravity coordinate map of fluorescence bright spots. Options (1) to (4) correspond to (A) to (D) in FIG. 4. FIG. 9 illustrates a state in which "Center of gravity coordinates" of option (4) is selected as an example. In this state, a map in which symbols indicating the coordinates of the center of gravity of the bright spots are arranged is displayed in the display area 71a where the segment image is displayed. Specifically, a map of the coordinates of the center of gravity of the first bright spot is displayed in the display area 71a corresponding to the first image. Although the display area 71a corresponding to the second image is hidden by the pull-down menu in FIG. 9, a map of the coordinates of the center of gravity of the second bright spot is displayed. In the image display area 74a of the analysis result field 74 where the composite image is displayed, the center-of-gravity coordinate maps of the first bright point and the second bright point are displayed.

Although only the state in which the option (4) is shown as an example in FIG. 9, when the option (2) is selected, the binarized image is displayed in the display areas 71a and 74a instead of the center of gravity coordinate map. When the option (3) is selected, the binarized image is displayed in the display areas 71a and 74a instead of the center of gravity coordinate map. When option (1) is selected, as shown in FIG. 8, the captured image before image processing is displayed in the display areas 71a and 74a instead of the center of gravity coordinate map.

Figure 10:
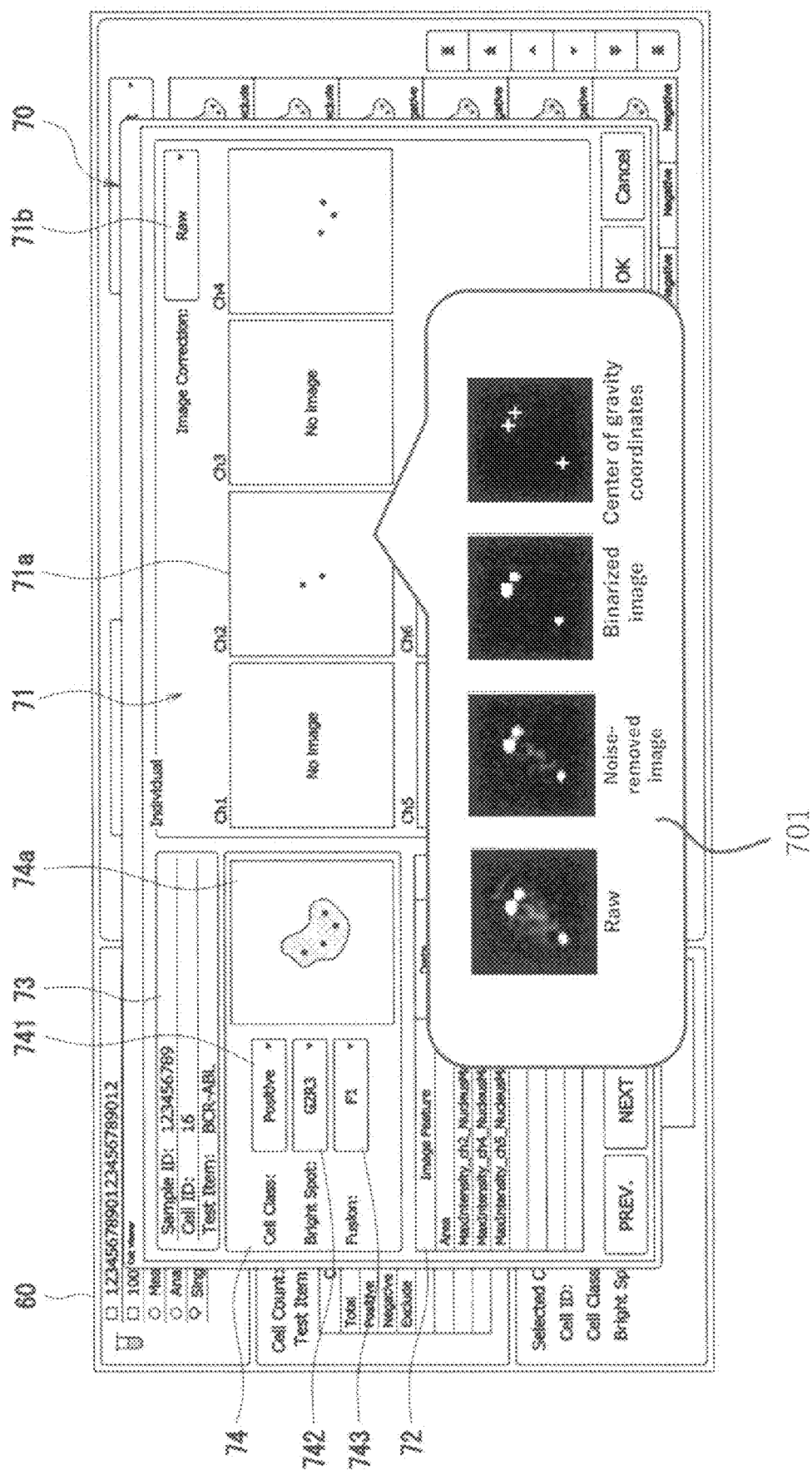
FIG. 10 is a diagram showing another display example of auxiliary information.

FIG. 9 shows an example in which the type of the image displayed in each of the display areas 71a and 74a is switched by operating the image type display unit 71b, but the display method is not limited to this. As shown in FIG. 10, depending on the selection of the images displayed in the display areas 71a and 74a, a plurality of images before and after image processing corresponding to the selected images, that is, the captured image (Raw) before image processing, the image after noise removal (Noise-removed image), the binarized image (Binarized image), and the center of gravity coordinates image (Center of gravity coordinates) may be displayed in a contrastable manner on one screen.

The auxiliary information field 72 displays information on the quality of the fluorescence image as auxiliary information. In the example of FIG. 8, the auxiliary information field 72 displays the area of cells included in the fluorescence image in units of the number of pixels. In the auxiliary information field 72, the maximum value of the brightness value of the fluorescence bright spot is displayed in the field of "Max Intensity_CHx_NucleusMask" for each of the first to third images (x=2, 4, 5). "Max Intensity_CH2_NucleusMask" means the maximum value of the brightness value in the fluorescence channel 2, and displays the highest brightness value in the image corresponding to the first green image. "Max Intensity_CH4_NucleusMask" means the maximum value of the brightness value in the fluorescence channel 4, and displays the highest brightness value in the image corresponding to the second image in red. "Max Intensity_CH5_NucleusMask" means the maximum value of the brightness value in the fluorescence channel 5, and displays the highest brightness value in the image corresponding to the third image corresponding to the nuclear staining. The maximum value of the brightness value in each segment image can be, for example, a material for determining whether the pretreatment is properly performed, and can be important information for assisting the visual analysis of cells. In the auxiliary information field 72, in addition to the brightness value of each segment image, the standard brightness obtained by experiment or the like, or the representative value of the brightness value of each fluorescence image acquired for the sample 20a is also displayed. In the auxiliary information field 72, instead of the absolute value of the brightness value, a relative value based on a representative value of the brightness of each fluorescence image or the like also may be displayed. In the auxiliary information field 72, the sum total of the luminance values in each segment image also may be displayed instead of the maximum luminance value.

Figure 14:
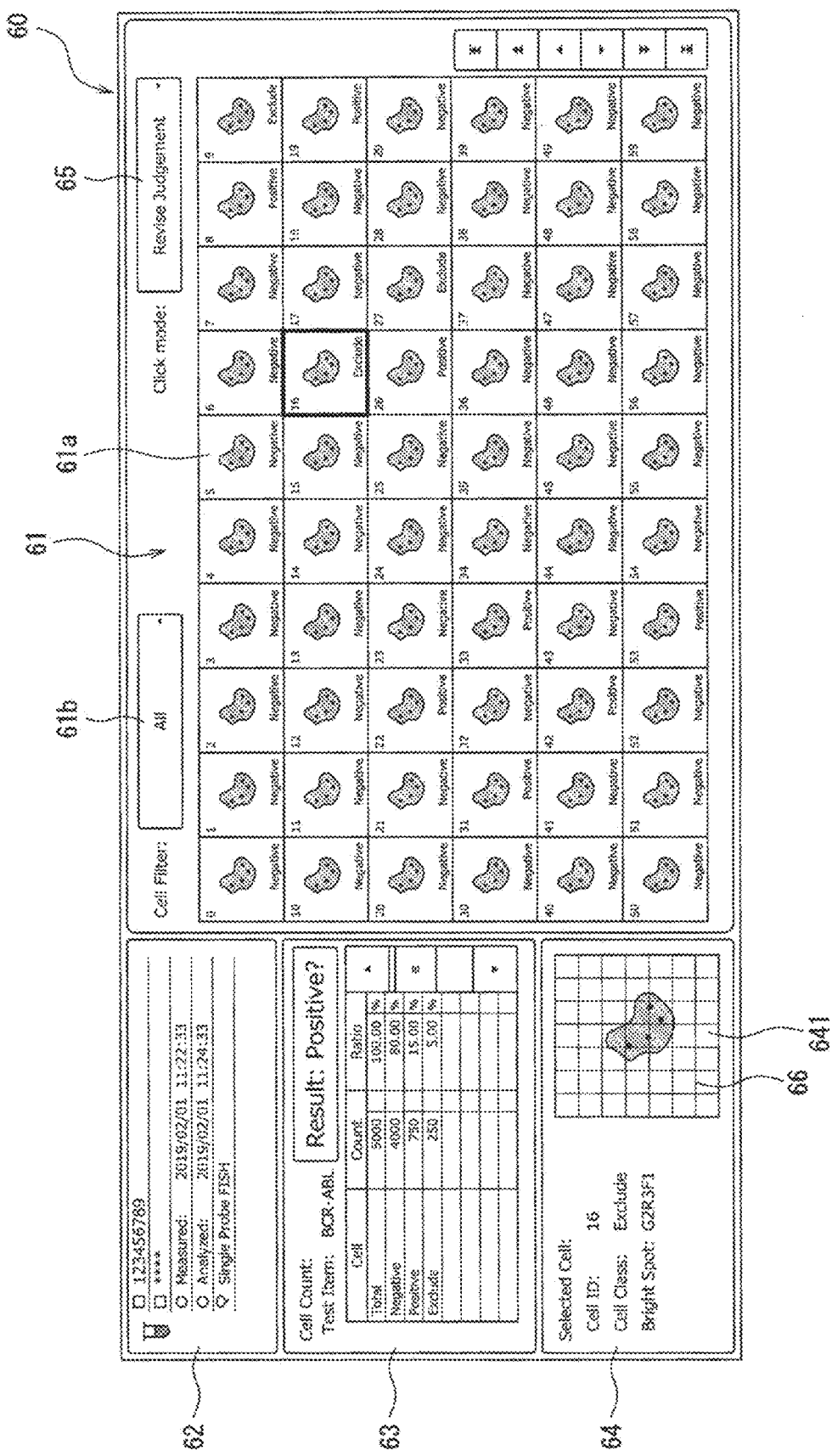
FIG. 14 is a diagram showing another display example of auxiliary information.

Although the pop-up display unit 70 is provided with auxiliary information fields 71 and 72, only one of them may be provided as auxiliary information for visual analysis. Further, the display screens of the auxiliary information fields 71 and 72 are not limited to the pop-up display unit 70 on the screen 60, and may be displayed by switching a part of the screen 60 as shown in FIG. 14 described later.

The information in the auxiliary information field 71 is particularly useful in the following cases. For example, even if the cell is determined to be a fusion of a first bright spot and a second bright spot by the fluorescence image analyzer 10, it is possible that it is not due to the fusion gene, but that the first bright spot and the second bright spot are aligned in the optical axis direction at the time of imaging. In this case, by observing the first image and the second image separately, it is possible to confirm whether the first bright spot and the second bright spot determined to be the fused bright spots are in focus or out of focus. If the operator determines the focus if off and it is not a fusion bright spot, the classification result can be corrected.

In another case, for example, the result of the fusion determination by the fluorescence image analyzer 10 may not match the result of the visual fusion determination. For example, in the fusion determination as described above, since the distances of the center of gravity coordinates are compared, there may be instances where the center of gravity coordinates are set at some distance from the position assumed by the operator due to the bright spots having a distorted shape, and as a result, it could be determined as a non-fused bright spot rather than the reverse. Although it is determined that the bright spot is not subject to cell classification because it has a distorted shape, there may be cases where it should be determined as a fusion bright spot. In such a case, the operator can confirm the shape of the bright spot by observing the first image and the second image separately, and can correct the classification result. Further, by operating the image type display unit 71b to check the images before and after the binarization process, it is possible to check, for example, whether the shape of the bright spot is extracted in a shape not expected by the operator.

In another case, for example, even a cell determined to be a negative cell by the fluorescence image analyzer 10 may be caused by the fact that the brightness of the first bright spot is significantly lower than that of the second bright spot. For example, the bright spots were not extracted in the binarization process due to the low brightness, but the bright spots may be visually confirmed. In this case, the operator observes the first image and the second image separately, or operates the image type display unit 71b to compare the images before and after the binarization process to verify the cause as inadequate staining. Alternatively, if the operator determines that the cause is poor staining by checking the brightness value of each fluorescence channel displayed in the auxiliary information field 72, the classification result is corrected from negative cells to positive cells, or the classification result can be modified to non-target.

Figure 11:
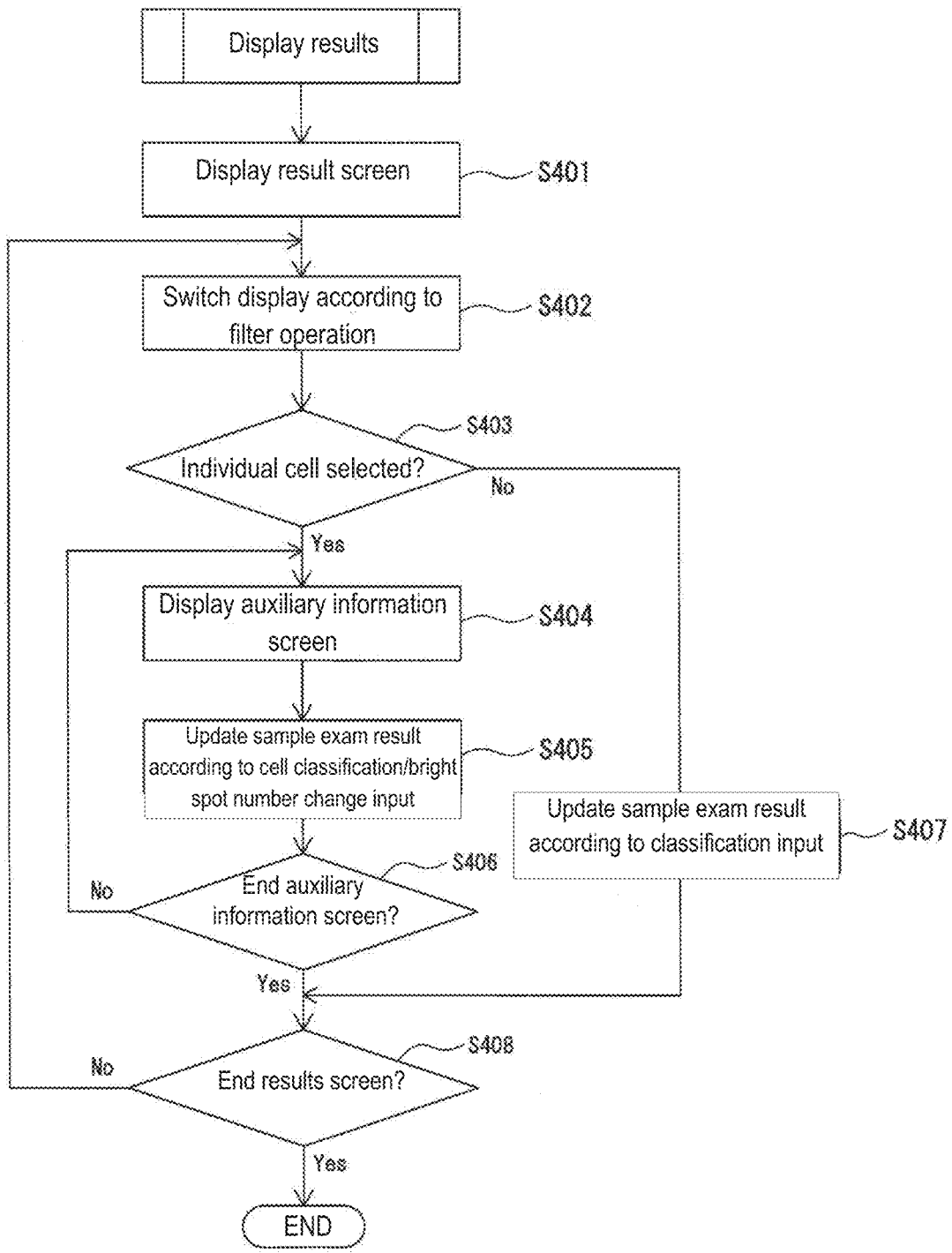
FIG. 11 is a flowchart showing an example of a result screen and an auxiliary information display process by a fluorescence image analyzer.

FIG. 11 is a flowchart showing an example of a process for displaying analysis results and auxiliary information. When the processor of the processing unit 11 executes the program stored in the storage unit 12, the process of displaying the screens shown in FIGS. 7 and 8 is executed.

In step S401, the processing unit 11 generates an analysis result of the sample 20a based on the result of classifying the cells, and then causes the display unit 13 to display a screen showing the analysis result. Specifically, as described with reference to FIG. 7, the processing unit 11 displays the screen 60 including identification information of the sample such as the sample ID, the number and ratio of cells of positive cells and negative cells for each pattern of fluorescence bright spots on the display unit 13.

In step S402, the processing unit 11 switches the display according to the filter operation of the operator. The operator can switch the image in the image display field 61 by operating the filter operation unit 61b on the screen 60, for example. The processing unit 11 executes a process of switching images based on the operation signal of the filter operation unit 61b. When the second option of displaying only the positive cell image is selected by the filter operation of the filter operation unit 61b, the processing unit 11 displays only the positive cell image in the image display field 61.

In step S403, the processing unit 11 determines whether one cell image has been selected by the operation of the operator. Specifically, the processing unit 11 determines whether the cell image (display cell 61a) in the image display field 61 of the screen 60 has been double-clicked. When the cell image is double-clicked, the processing unit 11 proceeds to step S404.

In step S404, the processing unit 11 causes the display unit 13 to display a pop-up screen 70 for displaying auxiliary information. As described above, a plurality of segment images are displayed in the auxiliary information field 71, and information regarding the fluorescence bright spot of each segment image is displayed in the auxiliary information field 72.

In step S405, when the operator changes the cell classification, the number of bright spots, and the like by operating the fields 741 to 743 of the analysis result field 74, the processing unit 11 then updates the exam result of the sample 20a according to the changed information. The operator can correct the cell classification result by, for example, checking the auxiliary information screen, performing a visual analysis of the cells, and operating fields 741 to 743 of the pop-up display unit 70. When the cell classification result is modified, the processing unit 11 updates the exam result of the sample 20a based on the changed classification result. For example, when the operator changes the classification of a cell automatically classified as a positive cell to a negative cell by operating field 741, 1 is subtracted from the number of positive cells in sample 20a and 1 is added to the number of negative cells. Along with this, the percentage of positive cells is recalculated. As a result of the recalculation, when the exam result of the sample 20a changes, for example, when it changes from positive to negative, the test result displayed on the exam result display unit 66 is similarly changed and displayed.

In step S406, the processing unit 11 determines whether the operation of closing the pop-up display unit 70, which is the auxiliary information screen, has been performed by the operation of the operator. When the operation is performed, the processing unit 11 ends the display of the pop-up display unit 70 and returns the screen 60 to the state of being the active window. If no operation is performed, the processing unit 11 repeats the processing of steps S404 and S405. In step S408, the processing unit 11 determines whether the operation of closing the screen 60 showing the analysis result has been performed by the operation of the operator. When the operation is performed, the processing unit 11 ends the display of the screen 60.

If the operation of calling the pop-up screen 70 is not performed in step S403, the processing unit 11 accepts the modification of the cell classification result by the operator's operation in step S407 while the screen 60 is displayed. If there is an input for changing the classification, the processing unit 11 updates the exam result of the sample 20a based on the changed classification result in the same manner as the processing described in S405 described above.

Modification Example 1

Figure 12:
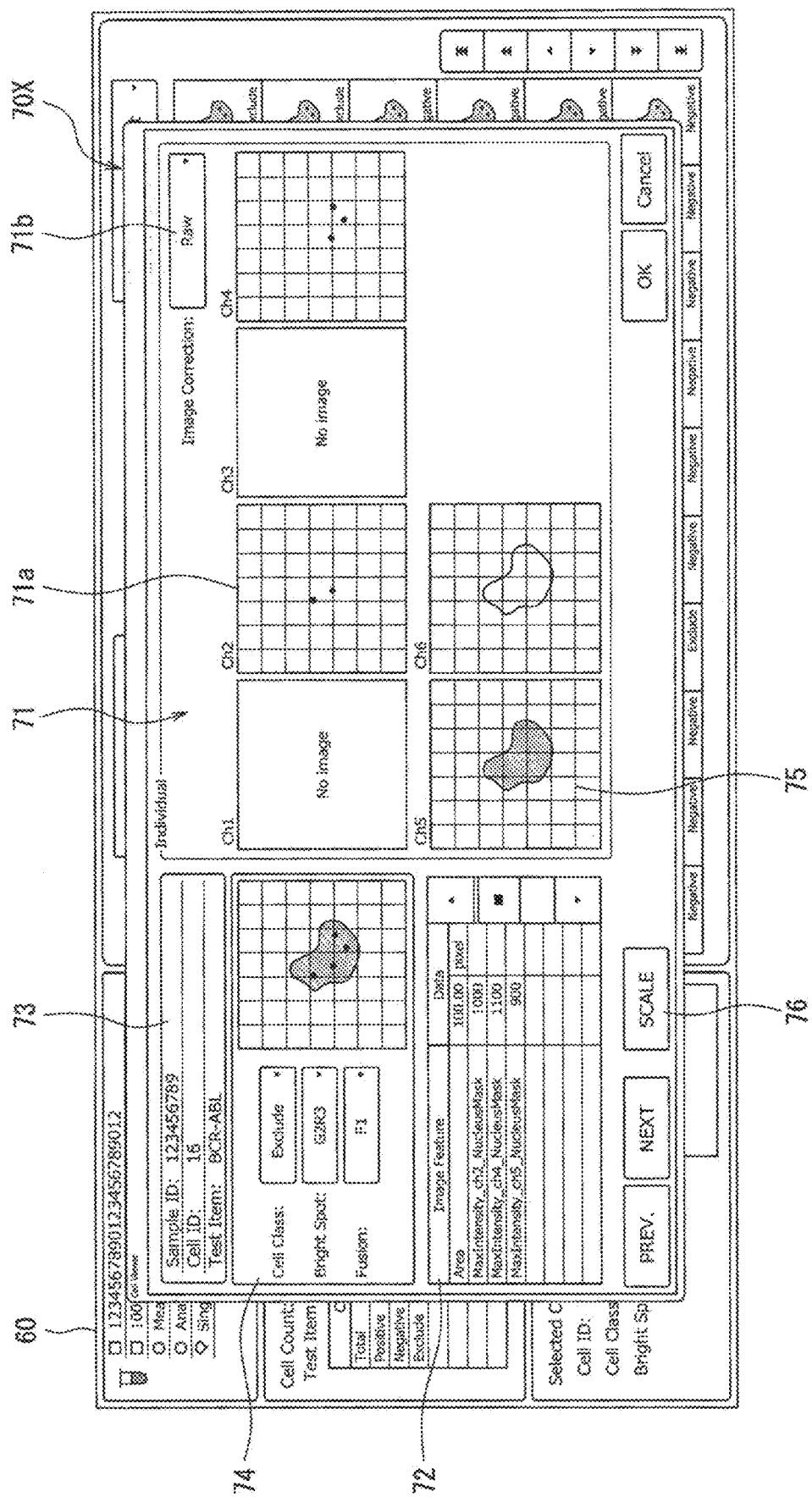
FIG. 12 is a diagram showing another display example of auxiliary information.

In the above embodiment, as auxiliary information, an image in which a composite image of cells is displayed in different modes, and more specifically, a segment image obtained by dividing a multicolor composite image into a plurality of elements and an image before and after image processing are displayed as an example. In the above embodiment, as another example of the auxiliary information, an example of displaying information on the quality of the image, specifically, numerical information of the maximum value of the brightness value of each segment image is shown. In the modification example 1, an example of displaying information visually added to the composite image of the cell as auxiliary information will be described. Specifically, as information for assisting the visual measurement of the distance between bright spots, an example of displaying a ruled line overlaid on a composite image of cells will be described. FIG. 12 is a diagram showing a pop-up display unit 70X which is a modification of the pop-up display unit 70. As shown in FIG. 12, the pop-up display unit 70X is common to the pop-up display unit 70 in the above-described embodiment in that it includes the auxiliary information fields 71 and 72, the basic information field 73, and the analysis result field 74. On the other hand, the pop-up display unit 70X differs from the pop-up display unit 70 in that a ruled line 75 is displayed in the image of the display area 71a. In the example shown in FIG. 12, the ruled line 75 is displayed in the first to third images and the bright field image of the auxiliary information field 71 and the composite image of the analysis result field 74.

The pop-up display unit 70X is provided with an operation unit 76 for turning on/off the display of the ruled line 75. Although the ruled line 75 may be displayed at all times, in the example shown in FIG. 12 the ruled line 75 is displayed based on the display request of the operator, in other words, based on the operation signal of the operation unit 76. The operator can display the ruled line 75 in the display area 71a and erase the ruled line 75 from the display area 71a by clicking, for example, the operation unit 76.

The ruled lines 75 are displayed at regular intervals along the vertical direction and the horizontal direction of the pop-up display unit 70X. The ruled lines 75 are displayed, for example, in all the display areas 71a at the same intervals and in the same positional relationship. The ruled line 75 also may be numbered to indicate a position, such as L1, L2, . . . , W1, W2, and so on. The ruled lines 75 having the same number are displayed at the same positions in each display area 71a.

The spacing between the ruled lines 75 is preferably determined based on the magnification of the image displaying the ruled lines 75, or based on the representative value of the size of the fluorescence bright spot. The interval between the ruled lines 75 is predetermined based on the magnification of the image, and when the image is enlarged or reduced, the interval between the ruled lines 75 also changes according to the magnification. Generally, the higher the magnification of the image, the smaller the spacing between the ruled lines 75. It is preferable that the pop-up display unit 70X displays a numerical value indicating the interval between the ruled lines 75. If the spacing between the ruled lines 75 is different in each display area 71a, a numerical value indicating the spacing is displayed for each display area 71a.

The spacing between the ruled lines 75 may be determined based on the average value, the median value, or the mode value, which is a representative value of the size of the fluorescence bright spot. The representative value also may be a value of a standard fluorescence bright spot size obtained by experiment or the like, or may be a value calculated from the fluorescence bright spot of each fluorescence image acquired for the sample 20a. The interval between the ruled lines 75 may be an integral multiple of the representative value of the size of the fluorescence bright spot, and when the image is enlarged or reduced, the magnification with respect to the representative value may be changed according to the magnification of the image.

The ruled line 75 is one of the auxiliary information for assisting the visual analysis of the cells, and is useful when the operator confirms the position and size of the fluorescence bright spots, the distance between the fluorescence bright spots, and the like. For example, when the operator determines the presence or absence of a fusion bright spot, the criterion is whether the two bright spots are separated by one bright spot. In the pop-up display unit 70X, the ruled line 75 is superimposed on the composite image displayed in the analysis result field 74 and the segment image displayed in the display area 71a, so that the operator can refer to the interval of the ruled line 75 to see the bright spots. The distance can be measured visually.

Figure 13:
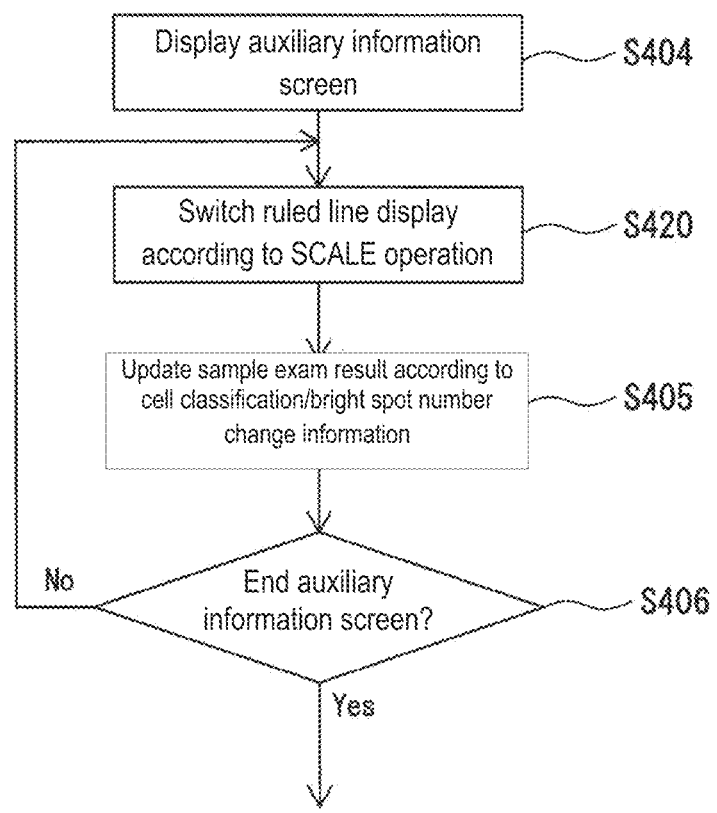
FIG. 13 is a flowchart showing an example of an auxiliary information display process by a fluorescence image analyzer.

FIG. 13 is a flowchart showing an example of an auxiliary information display process corresponding to the pop-up display unit 70X of FIG. 12. Since the flowchart of FIG. 13 is the same as the flowchart shown in FIG. 11 except that step S420 is added, only a portion of step S406 is extracted from step S404 of FIG. 11 and shown. As described with reference to FIG. 11, when one cell image is selected in the image display field 61 of the screen 60, the processing unit 11 causes the pop-up display unit 70X, which is an auxiliary information screen, to be displayed on the screen 60 (Step S404).

In step S420, the processing unit 11 switches the ruled line display according to the operation of the operation unit 76 (SCALE in FIG. 12) provided in the pop-up display unit 70X. As described above, the operation unit 76 is an operation unit for turning on/off the display of the ruled line 75, and the operator clicks the operation unit 76 to display the ruled line 75 in the display area 71a of the pop-up display unit 70X, and the ruled line 75 can be erased from the display area 71a. The processing unit 11 executes a process of switching the ruled line display based on the operation signal of the operation unit 76.

Subsequently, the processing unit 11 updates the exam result of the sample 20a based on the changed classification result (step S405). When the pop-up display unit 70X, which is an auxiliary information screen, is closed by the operation of the operator, the display of the pop-up display unit 70X also is terminated (step S406).

Modification Example 2

Although the ruled line 75 is displayed on the pop-up screen 70X that displays the detailed information of one cell in the Modification Example 1, as shown in FIG. 14, a ruled line 66 also may be displayed on the fluorescence image of the screen 60 that displays a plurality of composite images as thumbnails. In this case, since auxiliary information useful for visual analysis can be obtained without opening another screen such as the pop-up display units 70 and 70X, for example, the operator can hit the screen 60 to some extent, and usability is improved. In the example shown in FIG. 14, ruled lines 66 at regular intervals are displayed in the enlarged image 641 of the selected image display field 64.

Modification Example 3

Figure 15:
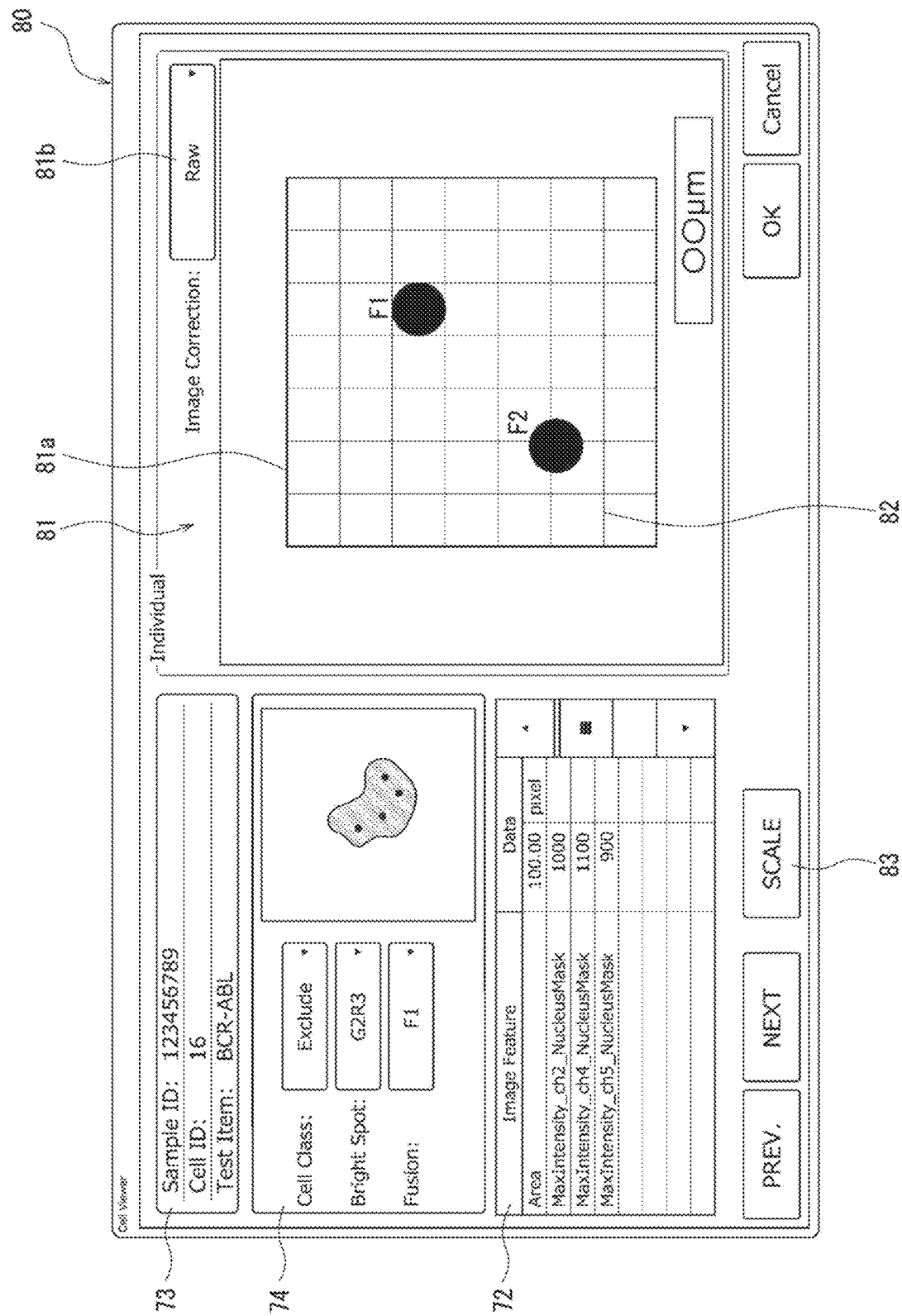
FIG. 15 is a diagram showing another display example of auxiliary information.

FIG. 15 is a diagram showing another example of the pop-up display unit 80 including the auxiliary information field 81. As shown in FIG. 15, the pop-up display unit 80 includes the auxiliary information field 72, the basic information field 73, and the analysis result field 74, and the display other than the auxiliary information field 81 is the same as that of the pop-up display unit 70X. The auxiliary information field 81 is provided with a display area 81a for displaying a fluorescence image and an image type display unit 81b. Similar to the image type display unit 71b, the image type display unit 81b also functions as an operation unit that displays the type of the image being displayed in the display area 81a and enables switching of the images. In the example shown in FIG. 15, the captured image "Raw" before image processing is selected.

Although one display area 81a is provided in the auxiliary information field 81, there may be a plurality of display areas 81a. A composite image of the first to third images is displayed in the display area 81a, and ruled lines 82 at regular intervals are displayed in the composite image. The ruled line 82 is useful for confirming the position and size of the fluorescence bright spots, the distance between the fluorescence bright spots, and the like, and is displayed with the same settings as the ruled line 75 of the pop-up display unit 70X. The pop-up display unit 80 is provided with an operation unit 83 for turning on/off the display of the ruled line 82.

The composite image displayed in the display area 81a is the same as that displayed in the analysis result field 74, but the image can be enlarged in the display area 81a. The operator can magnify a part of the nuclear region in the display region 81a to check the shape and size of the fluorescence bright spots, the distance between the fluorescence bright spots, and the like. In the example shown in FIG. 15, the region where the first bright spot F1 and the second bright spot F2 are close to each other is enlarged and displayed. In the auxiliary information field 81, a numerical value indicating the interval between the ruled lines 82 also is displayed. Note that the image displayed in the display area 81a is not limited to the composite image of the first to third images, and may be a composite image of the first image and the second image, and may be selectable by the operator.

Other Modification Examples

Figure 16:
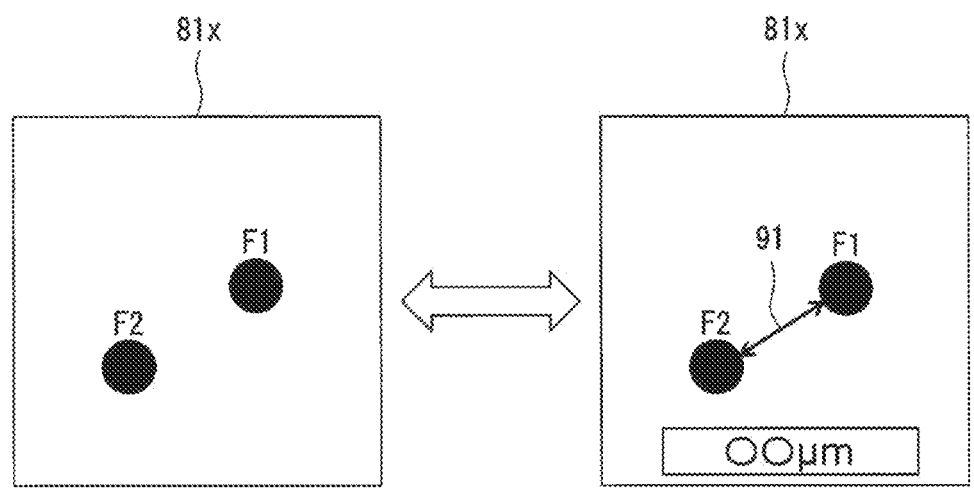
FIG. 16 is a diagram showing another display example of auxiliary information.
Figure 17:
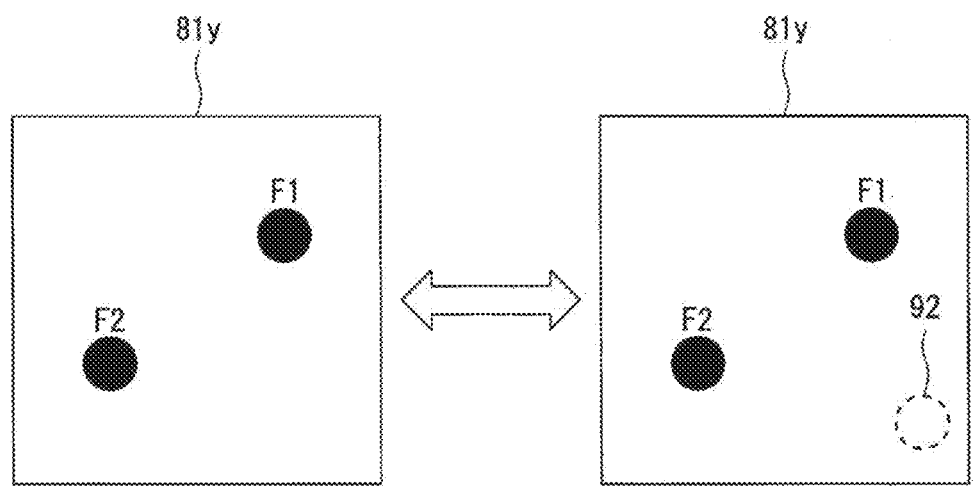
FIG. 17 is a diagram showing another display example of auxiliary information.
Figure 18:
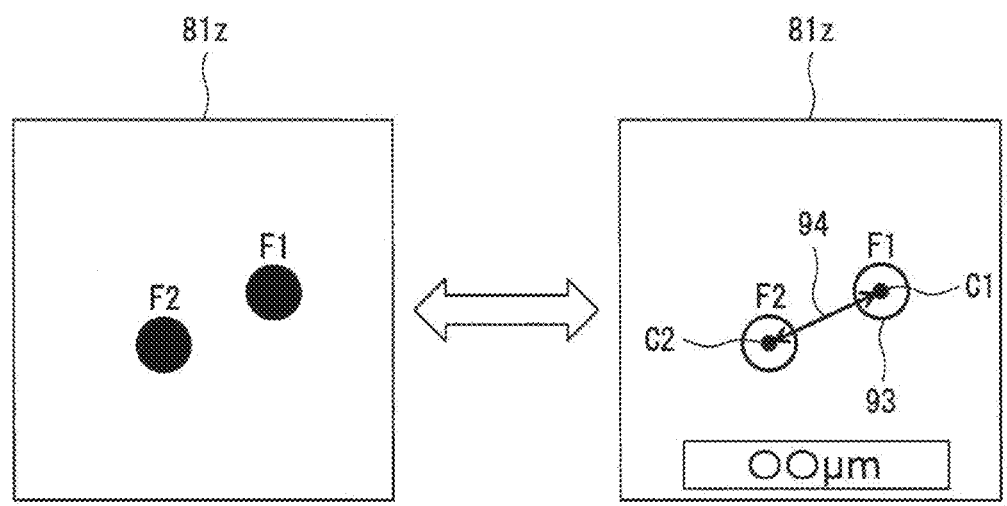
FIG. 18 is a diagram showing another display example of auxiliary information.

FIGS. 16 to 18 are diagrams showing other examples of auxiliary information displayed in the fluorescence image of the auxiliary information field 81. Similar to the display area 81a shown in FIG. 15, the first bright spot F1 and the second bright spot F2 of the nuclear region of the composite image near the display regions 81x to 81z are displayed enlargements.

As shown in FIG. 16, in the display region 81x, distance information 91 indicating the distance between the fluorescence bright spots is displayed as auxiliary information for assisting the visual analysis of the cells. The distance information 91 includes an arrow extending straight from the first bright spot F1 to the second bright spot F2 and indicating the distance between the bright spots. In the display area 81x, the length of the arrow, that is, the distance between the fluorescence bright spots also is displayed. In the example shown in FIG. 16, an arrow is displayed so as to connect the points where the outer circumferences of the two fluorescence bright spots are nearest to each other.

The distance between the fluorescence bright spots indicated by the distance information 91 is the distance between the points where the outer circumferences of the two fluorescence bright spots are nearest each other, or the distance between the centers of gravity or the center points of the two fluorescence bright spots. In the example shown in FIG. 16, as described above, the distance between the outer circumferences of the two fluorescence bright spots that are nearest each other is displayed. In the display area 81x, as the distance information 91, all of the distance between the points where the outer circumferences of the two fluorescence bright spots are nearest each other, the distance between the centers of gravity, and the distance between the center points may be displayed, and the display distance may be switched by the operator.

As shown in FIG. 17, the reference bright spot 92 is displayed in the display region 81y as auxiliary information for assisting the visual analysis of the cells. The reference bright spot 92 is a circle corresponding to one of the fluorescence bright spots. The size of the circle corresponding to one of the fluorescence bright spots is determined based on the representative value of the size of the fluorescence bright spot. The representative value is an average value, a median value, or a mode value, and may be a value of a standard fluorescence bright spot size obtained by experiment or the like, and is a value of each fluorescence image acquired for the sample 20a. It may be a value calculated from the fluorescence bright spot. By displaying the reference bright spot 92, the shape, size, distance between the fluorescence bright spots, and the like can be compared with the typical fluorescent bright spots.

Although in the example shown in FIG. 17 one reference bright spot 92 is displayed by a broken line at the lower right of the display area 81y, the display form of the reference bright spot 92 is not particularly limited, and a circle or a circle may be displayed by a solid line or a colored circle. The number of the reference bright spots 92 is not limited to one, and one may be displayed corresponding to the first bright spot F1 and the second bright spot F2. The display position of the reference bright spot 92 also may be between the first bright spot F1 and the second bright spot F2. The reference bright spot 92 may be movable, or may be movable by dragging the reference bright spot 92 to an optional place in the display area 81y.

As shown in FIG. 18, in the display region 81z, a contour line 93 that emphasizes the contour of the fluorescence bright spot is displayed as auxiliary information for assisting the visual analysis of the cells. The contour line 93 is displayed at the first bright point F1 and the second bright point F2, respectively. Although in the example shown in FIG. 18 the contour line 93 is displayed as a solid line, the display form of the contour line 93 is not particularly limited and may be displayed as a broken line. The contour line 93 is displayed along the contour of the fluorescence bright spot extracted by the binarization process. By displaying the contour line 93, for example, when the contour of the fluorescence bright spot is not clear, it becomes easy to confirm the shape, size, distance between the fluorescence bright spots, and the like.

In the display area 81z, in addition to the contour line 93, the center of gravity C1 of the first bright point F1 and the center of gravity C2 of the second bright point F2 are displayed. The centers of gravity C1 and C2 are those used for the fusion determination and are calculated from the binarized image. Further, in the display area 81z, an arrow indicating the distance between the centers of gravity and the distance information 94 including the length of the arrow are displayed. Note that in the display area 81z, the center point of the fluorescence bright spot may be displayed together with or instead of the contour line 93 and the centers of gravity C1 and C2.

As described above, examples of auxiliary information that assists in the visual analysis of cells based on fluorescence bright spots are at least one selected from information on the position, shape, size, brightness, and distance between fluorescence bright spots. Specific examples include: a) a ruled line at regular intervals, b) a circle corresponding to one of the fluorescence bright spots, c) a display emphasizing at least one of the outline, the center of gravity, and the center point of the fluorescence bright spot, and d) a display showing the distance between the fluorescence bright spots. The auxiliary information regarding the fluorescence bright spot includes information on the segment image constituting the composite image and information on image processing. This information can be an important determining index for the operator to perform a visual analysis.

The processing unit 11 may display one of the auxiliary information described above, or may selectively combine and display a plurality of auxiliary information. As an example, it is possible to add a display that emphasizes at least one of the outline, the center of gravity, and the center point of the fluorescence bright spot as shown in FIG. 18 on the image on which the auxiliary information of FIGS. 8, 12, and 14 to 17 is displayed.

According to the above-described embodiment, many fluorescent images are acquired for each cell by the FISH method using the flow cell 110, the images undergo image processing and image analysis by software, and each cell is automatically classified into positive cell and negative cell. A function also is provided to classify fluorescence images that are not suitable for cell classification by software into non-targets. Then, at least the non-target cells can be visually analyzed by the operator, and auxiliary information for assisting the visual analysis is provided. In this way visual analysis by the operator is facilitated, so that the classification accuracy is improved and the influence of the operator's skill level on the inspection result is suppressed.

When the operator performs a visual analysis, a fluorescence image of the cells, the result of automatic classification, and auxiliary information to assist the visual analysis of the cell based on the fluorescence bright spot are provided. Auxiliary information may be collectively displayed for all fluorescence images regardless of the operator's selection, but preferably, auxiliary information is displayed for a specific image selected from the fluorescence images. Although the specific image is at least a non-target cell image, the positive cell image and the negative cell image may also display auxiliary information based on, for example, an operator's selection operation. The auxiliary information may be any information useful for visual analysis of cells. As described above, the auxiliary information includes at least one selected from information on the position, shape, size, brightness, and distance between the fluorescence bright spots, and at least one display enhancement of ruled lines at regular intervals, contours of fluorescence bright spots, a center of gravity, and center points. In addition, the auxiliary information may include information on segment images constituting the composite image and information on image processing.

Of the several auxiliary information options described above, particularly information that assists in the visual measurement of the distance between bright spots, ruled lines (FIG. 12, FIG. 14, FIG. 15), information on distance between bright spots (FIG. 16), shape for comparison and control of distance between bright spots (FIG. 17), and emphasis on contour, center of gravity or center point of fluorescent bright spot in the display (FIG. 18) is not an alternative and may be displayed in overlay. The visual measurement of the distance between bright spots depends on the skill level of the operator as described above. So, for example, a situation may arise wherein a less skilled operator wants to display multiple auxiliary information options, while a more skilled operator wants to perform visual analysis based on skill and intuition without relying on auxiliary information. In such a case, it is convenient to be able to set which of the auxiliary information options to display and how to display it for each operator. Therefore, as shown in FIG. 19, it is preferable to store the setting of the auxiliary information option in the storage unit 12 in association with the operator ID.

The example shown in FIG. 19 shows a database in which the operator ID is associated with the settings for turning ON/OFF the ruled lines, the information display of the distance between bright spots is turned on/off, the figure for comparison and control of the distance between bright spots is turned on/off, the outline highlighting of fluorescent bright spots is turned on/off, and whether the center of gravity or the center point is set as the method of specifying the bright spot coordinates. The processing unit 11 refers to the database based on the ID of the operator who has logged in to the fluorescence image analyzer 10, reads out the auxiliary information option setting, and displays the fluorescence image according to the setting. With this configuration, the operator does not have to change the auxiliary information option according to his/her preference each time he/she logs in, which is preferable.

Note the present invention is not limited to the above-described embodiments and modifications, and the design can be appropriately changed insofar as the object of the present invention is not impaired. For example, the cells included in the image may be classified into positive cells and negative cells based on the number of fluorescence bright spots without performing the fusion determination of the fluorescence bright spots. Since the cell classification method, that is, the index used for classification differs depending on the cell to be analyzed, the target site, the measurement item, the fluorescent label and the like, it is necessary to use an appropriate classification index according to the analysis target.

Figure 20:
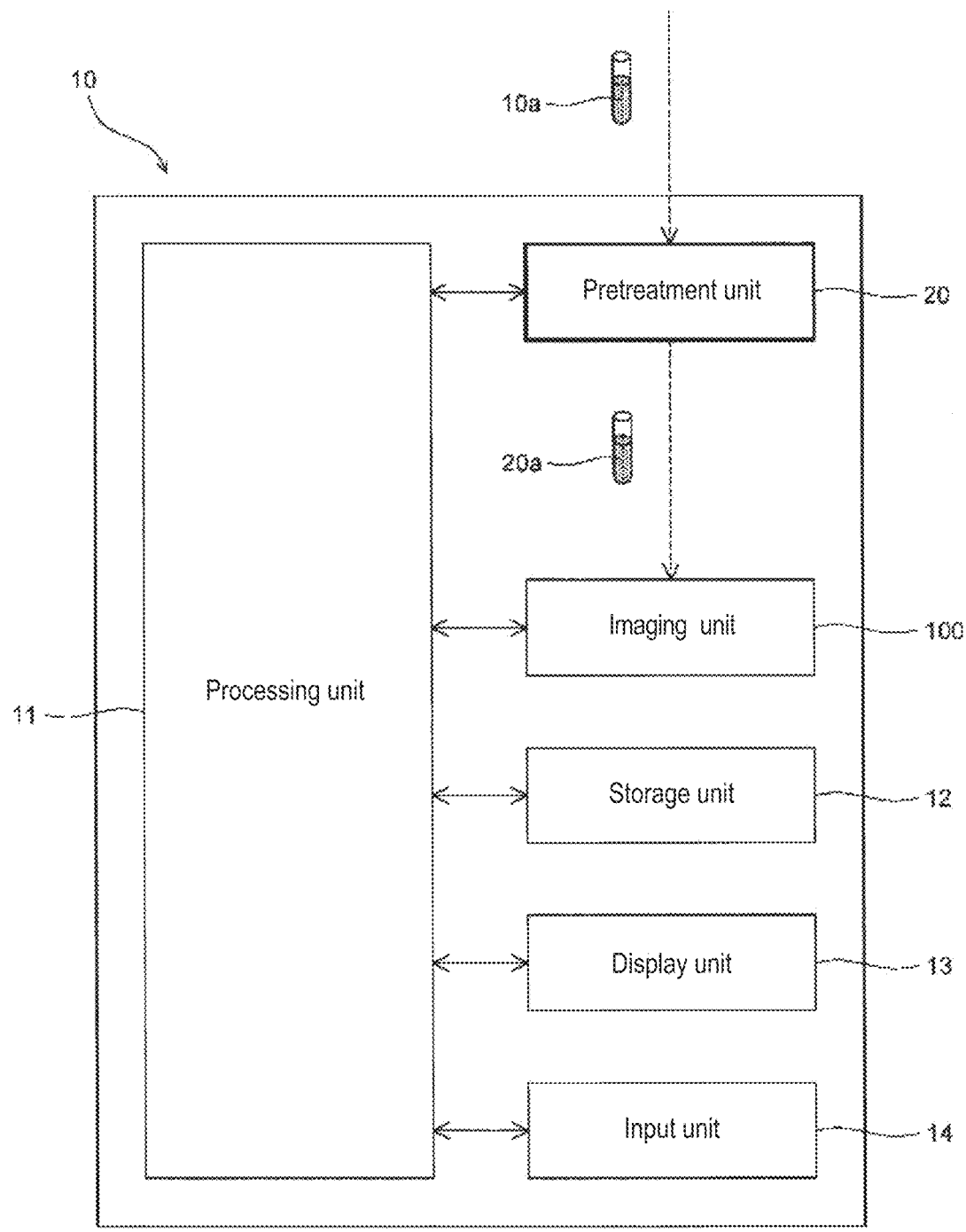
FIG. 20 is a schematic view of a fluorescence image analyzer which is another example of the embodiment.

As shown in FIG. 20, the fluorescence image analyzer 10 may include a pretreatment unit 20 in the apparatus. The processing unit 11 is connected to the preprocessing unit 20 and is configured to be capable of controlling the preprocessing unit 20. When the sample 10*a* collected from the subject and subjected to treatment such as centrifugation is set, the pretreatment unit 20 preprocesses the sample 10*a* and prepares the sample 20*a* containing cells having a fluorescently labeled target site. Note that the other structures are the same as those shown in FIG. 1. When the fluorescence image analyzer 10 includes the pretreatment unit 20 as illustrated in FIG. 20, the operator simply sets the sample 10*a* in the device, and the pretreatment is automatically performed, and the prepared sample 20*a* is automatically analyzed.

Figure 21:
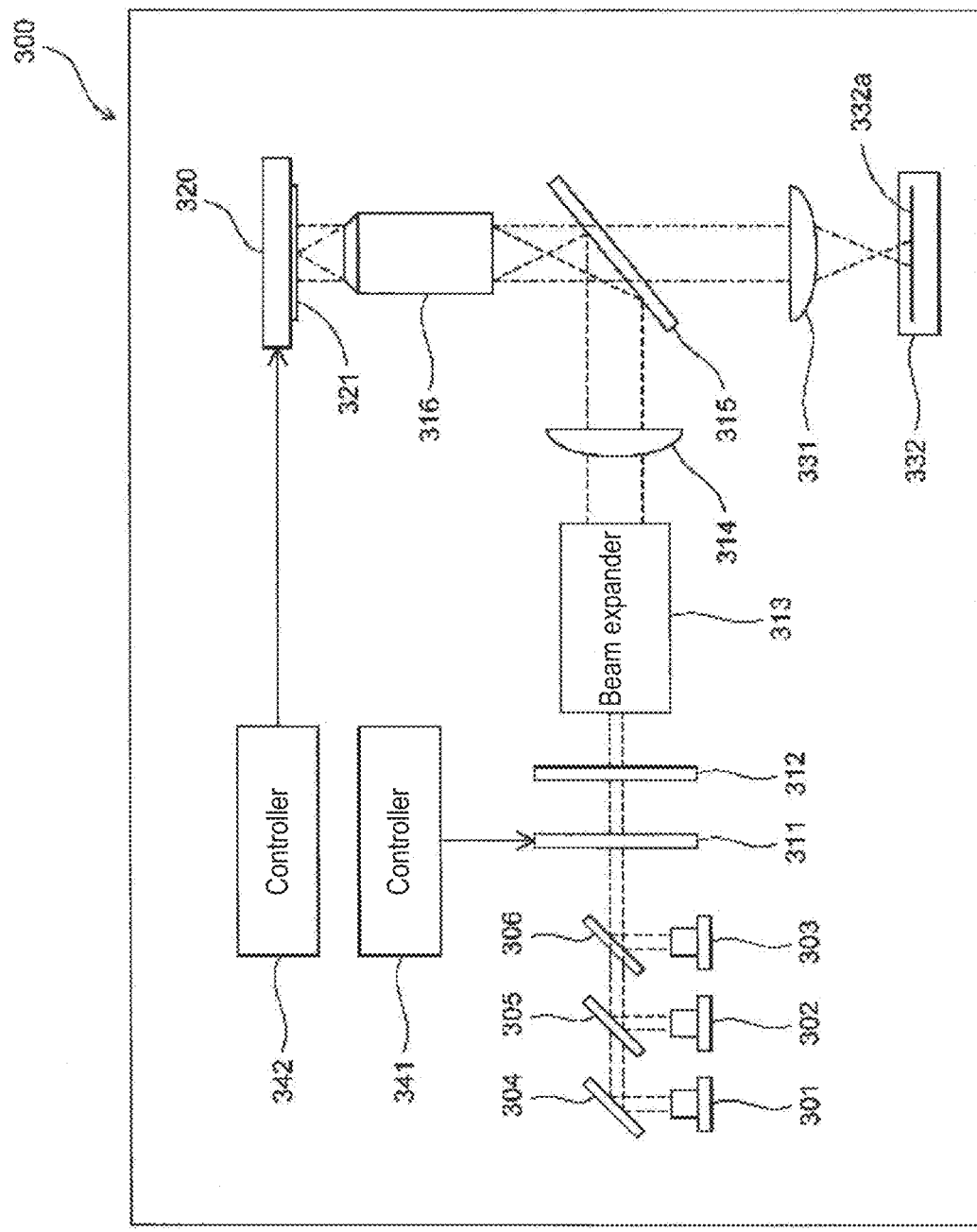
FIG. 21 is a schematic view of a fluorescence image analyzer which is another example of the embodiment.

As shown in FIG. 21, as the imaging unit of the fluorescence image analyzer, an imaging unit 300 including a fluorescence microscope may be provided instead of the imaging unit 100 illustrated in FIG. 1. The imaging unit 300 includes light sources 301 to 303, mirrors 304, dichroic mirrors 305 and 306, shutter 311 and ¼ wavelength plate 312, beam expander 313, condensing lens 314, and dichroic mirror 315, objective lens 316, stage 320, condenser lens 331, image pickup unit 332, and the controllers 341 and 342.

The stage 320 is a support base on which the slide glass 321 is installed, and is driven by the controller 342. The sample 20*a* prepared by the pretreatment unit 20 is placed on the slide glass 321 installed on the stage 320. That is, in the imaging unit 300, the fluorescence-labeled cells on the slide glass 321 are imaged by a fluorescence microscope provided with the image pickup unit 332, and a fluorescence image is acquired. In this case as well, a composite image of the first to third images can be obtained as the fluorescence image.

The light sources 301 to 303 are the same as the light sources 121 to 123 shown in FIG. 1, respectively. The mirror 304 reflects the light from the light source 301. The dichroic mirror 305 transmits the light from the light source 301 and reflects the light from the light source 302. The dichroic mirror 306 transmits the light from the light sources 301 and 302 and reflects the light from the light source 303. The optical axes of the light from the light sources 301 to 303 are aligned with each other by the mirror 304 and the dichroic mirrors 305 and 306.

The shutter 311 is driven by the controller 341 and switches between a state in which the light emitted from the light sources 301 to 303 is passed through and a state in which the light emitted from the light sources 301 to 303 is blocked. In this way the irradiation time of the light on the sample 20a is adjusted. The quarter wave plate 312 converts the linearly polarized light emitted from the light sources 301 to 303 into circularly polarized light. The fluorescent dye bound to the nucleic acid probe reacts with light in a predetermined polarization direction. Therefore, by converting the excitation light emitted from the light sources 301 to 303 into circularly polarized light, the polarization direction of the excitation light can easily match the polarization direction in which the fluorescent dye reacts. In this way it possible to efficiently excite the fluorescent dye.

The beam expander 313 expands the light irradiation area on the slide glass 321. The condenser lens 314 collects light so that the slide glass 321 is irradiated with parallel light from the objective lens 316. The dichroic mirror 315 reflects the light emitted from the light sources 301 to 303 and transmits the fluorescence generated from the sample 20a. The objective lens 316 guides the light reflected by the dichroic mirror 315 to the slide glass 321.

The fluorescence generated from the sample 20a passes through the objective lens 316 and passes through the dichroic mirror 315. The condenser lens 331 collects the fluorescence transmitted through the dichroic mirror 315 and guides it to the imaging surface 332a of the imaging unit 332. The image pickup unit 332 captures an image of fluorescence irradiated on the imaging surface 332a and generates a fluorescence image. The image pickup unit 332 is composed of, for example, a CCD or the like.

The controllers 341 and 342 and the imaging unit 332 are connected to the processing unit 11 described above. The processing unit 11 controls the controllers 341 and 342 and the imaging unit 332, and receives the fluorescence image captured by the imaging unit 332. Note that the fluorescence image captured by the image pickup unit 332 may have cells in close contact with each other as shown in FIG. 2A, unlike the case where the flow cell 110 is used. Therefore, the processing unit 11 performs a process of dividing the acquired fluorescence image into each cell nucleus, a process of setting a region corresponding to the nucleus of one cell in the fluorescence image, and the like.

Even in the fluorescence image analyzer provided with the imaging unit 300, the cells are automatically classified based on the fluorescence bright spots of the acquired fluorescence image. Then, the fluorescence image of the cells, the result of the automatic classification, and the auxiliary information that assists the visual classification of the cells based on the fluorescence bright spot are displayed. As described above, the present invention is also applicable to the automated slide FISH method.

What is claimed is:

1. A fluorescence image display method comprising:
    obtaining a fluorescence image by imaging an individual cell having target sites labeled with first and second fluorescence dyes of first and second colors;
    performing image analysis via software based on first and second fluorescence bright spots included in the fluorescence image, the first and second fluorescence bright spots respectively corresponding to the first and second colors; and
    displaying the fluorescence image, the results of the image analysis of the fluorescence image, and auxiliary information that assists visual analysis of the first and second fluorescence bright spots included in the fluorescence image of the individual cell, wherein the auxiliary information includes information that assists a visual measurement of a distance between the first and second fluorescence bright spots in the individual cell.

2. The fluorescence image display method according to claim 1, wherein
    the image analysis includes classifying the cells based on the fluorescence bright spots contained in the fluorescence image.

3. The fluorescence image display method according to claim 2, wherein
    the image analysis includes identifying a fluorescence image that is not subject to cell classification by the software.

4. The fluorescence image display method according to claim 3, wherein
    the result of the image analysis includes information for identifying a fluorescence image that is not subject to cell classification by the software.

5. The fluorescence image display method according to claim 1, wherein
    the result of the image analysis includes the cell classification result given to the fluorescence image of the cell for which the cell classification based on the fluorescence bright spots is performed by the software.

6. The fluorescence image display method according to claim 1, wherein
    the auxiliary information includes information that assists visual analysis of whether two fluorescence bright spots included in the fluorescence image are fused.

7. The fluorescence image display method according to claim 1, further comprising:
    displaying an operation unit for changing the result of the image analysis of the fluorescence image by the software together with the fluorescence image and the auxiliary information, and changing the result of the image analysis in response to an input via the operation unit.

8. The fluorescence image display method according to claim 1, wherein
    the auxiliary information further includes an image displayed in a different manner than the fluorescence image, or information regarding the quality of the fluorescence image.

9. The fluorescence image display method according to claim 8, wherein
    the auxiliary information is at least one selected from among
    a) ruled lines at regular intervals displayed overlaid on the fluorescence image;
    b) figure corresponding to one fluorescence bright spot;
    c) display that emphasizes at least one of the contour, center of gravity, and center point of the fluorescence bright spot;
    d) display showing the distance between the fluorescence bright spots.

10. The fluorescence image display method according to claim 8, wherein
    the information regarding the quality of the fluorescence image is information obtained by quantifying the brightness of the fluorescence image.

11. The fluorescence image display method according to claim 8, wherein
    as the auxiliary information, the maximum value of the brightness value of a first color and the maximum value of the brightness value of a second color included in the fluorescence image are displayed.

12. The fluorescence image display method according to claim 8, wherein
the fluorescence image comprises a color image including a plurality of color elements; and
the image obtained by displaying the fluorescence image in different modes is a plurality of element images obtained by dividing the multicolor image into a plurality of monochromatic element images.

13. The fluorescence image display method according to claim 8, wherein
the fluorescent image includes a first image showing a first bright spot, a second image showing a second bright spot, a third image showing the fluorescence of the nuclear staining dye that labels the nucleus of the cell, and a composite image in which the first through third images are combined; and
the composite image is divided into the first image, the second image, and the third image and displayed as images in which the fluorescence image is displayed in different modes.

14. The fluorescence image display method according to claim 12, further comprising:
displaying a list of composite images of multiple cells; and
dividing a selected composite image into a first image, a second image, and a third image according to the selection of one composite image from the plurality of composite images displayed in the list, and displaying the first image, the second image, and the third image.

15. The fluorescence image display method according to claim 8, wherein
the image analysis includes image processing the fluorescent image to create a processed image; and
the processed image and the fluorescence image are displayed in a contrastable manner as images in which the fluorescence image is displayed in different modes.

16. The fluorescence image display method according to claim 1 further comprising:
classifying the fluorescence image into at least a fluorescence image of normal cells, a fluorescence image of abnormal cells, and a fluorescence image of non-target cells by the image analysis.

17. The fluorescence image display method according to claim 1, wherein
the fluorescence image is obtained by forming a sample stream containing the cells in a flow cell and imaging the cells in the sample.

18. The fluorescence image display method according to claim 1, wherein
the fluorescent bright spots include a first fluorescent spot emitted by a first fluorescent dye that labels a first target site of the cell, and a second fluorescent spot that is emitted by a second fluorescent dye that labels a second target site of the cell.

19. The fluorescence image display method according to claim 9, wherein
the interval between the ruled lines is determined based on the magnification of the fluorescence image displaying the ruled lines or based on a representative value of the size of the fluorescent bright spot.

20. The fluorescence image display method according to claim 9, wherein
the size of the figure corresponding to one of the fluorescent bright spots is determined based on a representative value of the size of the fluorescent bright spot.

21. The fluorescence image display method according to claim 9, wherein
the distance between the fluorescent bright spots is the distance between the points at which the outer circumferences of the two fluorescent bright spots are closest to each other, or the distance between the centers of gravity, or the center points of the two fluorescent bright spots.

22. The fluorescence image display method according to claim 1, further comprising:
displaying the auxiliary information based on the identification information of the operator and the information related to the setting of the auxiliary information stored in association with the identification information of the operator.

23. A fluorescence image analyzer comprising:
a light source that irradiates cells having a target site labeled with a fluorescent dye;
an imaging unit that acquires a fluorescence image of an individual cell that emits fluorescence when irradiated with light from the light source;
a processing unit that analyzes the fluorescence image based on first and second fluorescent bright spots included in the fluorescence image, the first and second fluorescence bright spots respectively corresponding to first and second colors;
a display unit;
wherein the processing unit is configured to display the fluorescence image of the cells, the result of the image analysis, and auxiliary information includes information that assists a visual measurement of a distance between the first and second fluorescence bright spots in the individual cell.

* * * * *